US011369655B2

(12) United States Patent
George et al.

(10) Patent No.: US 11,369,655 B2
(45) Date of Patent: Jun. 28, 2022

(54) HEALTHFUL SUPPLEMENTS

(71) Applicant: CG-Bio Genomics, Inc., Farmington, ME (US)

(72) Inventors: Marc J. George, Grand Haven, MI (US); William C. Carrington, Grand Haven, MI (US)

(73) Assignee: CG-Bio Genomics, Inc., Farmington, ME (US)

( * ) Notice: Subject to any disclaimer, the term of this patent is extended or adjusted under 35 U.S.C. 154(b) by 912 days.

(21) Appl. No.: 15/742,242

(22) PCT Filed: Jul. 6, 2016

(86) PCT No.: PCT/US2016/041161
§ 371 (c)(1),
(2) Date: Jan. 5, 2018

(87) PCT Pub. No.: WO2017/007833
PCT Pub. Date: Jan. 12, 2017

(65) Prior Publication Data
US 2018/0193403 A1 Jul. 12, 2018

Related U.S. Application Data

(60) Provisional application No. 62/189,087, filed on Jul. 6, 2015.

(51) Int. Cl.
| | | |
|---|---|---|
| A61K 36/9066 | (2006.01) |
| A61K 36/185 | (2006.01) |
| A23L 33/105 | (2016.01) |
| A61K 36/889 | (2006.01) |
| A61K 36/07 | (2006.01) |
| A61K 36/324 | (2006.01) |
| A61K 36/71 | (2006.01) |
| A61P 35/00 | (2006.01) |
| A23L 33/115 | (2016.01) |
| A23L 2/52 | (2006.01) |
| A61K 31/01 | (2006.01) |
| A61K 31/015 | (2006.01) |
| A61K 31/045 | (2006.01) |
| A61K 31/047 | (2006.01) |
| A61K 31/05 | (2006.01) |
| A61K 31/19 | (2006.01) |
| A61K 31/192 | (2006.01) |
| A61K 31/198 | (2006.01) |
| A61K 31/20 | (2006.01) |
| A61K 31/352 | (2006.01) |
| A61K 31/401 | (2006.01) |
| A61K 31/405 | (2006.01) |
| A61K 31/4172 | (2006.01) |
| A61K 36/074 | (2006.01) |
| A61K 36/23 | (2006.01) |
| A61K 36/282 | (2006.01) |
| A61K 36/48 | (2006.01) |
| A23L 33/10 | (2016.01) |

(52) U.S. Cl.
CPC ............ *A61K 36/9066* (2013.01); *A23L 2/52* (2013.01); *A23L 33/105* (2016.08); *A23L 33/115* (2016.08); *A61K 31/01* (2013.01); *A61K 31/015* (2013.01); *A61K 31/045* (2013.01); *A61K 31/047* (2013.01); *A61K 31/05* (2013.01); *A61K 31/19* (2013.01); *A61K 31/192* (2013.01); *A61K 31/198* (2013.01); *A61K 31/20* (2013.01); *A61K 31/352* (2013.01); *A61K 31/401* (2013.01); *A61K 31/405* (2013.01); *A61K 31/4172* (2013.01); *A61K 36/07* (2013.01); *A61K 36/074* (2013.01); *A61K 36/185* (2013.01); *A61K 36/23* (2013.01); *A61K 36/282* (2013.01); *A61K 36/324* (2013.01); *A61K 36/48* (2013.01); *A61K 36/71* (2013.01); *A61K 36/889* (2013.01); *A61P 35/00* (2018.01); *A23L 33/10* (2016.08); *A23V 2002/00* (2013.01)

(58) Field of Classification Search
None
See application file for complete search history.

(56) References Cited

U.S. PATENT DOCUMENTS

2005/0238655 A1   10/2005   Stamets
2009/0252796 A1   10/2009   Mazed et al.
(Continued)

FOREIGN PATENT DOCUMENTS

EP   2444081   4/2012
GB   2478595   9/2011
(Continued)

OTHER PUBLICATIONS

Andrew, et al., British Journal of Pharmacology, 174:1177. (Year: 2017).*
Yao, et al., Journal of Ethnopharmacology, 150:619. (Year: 2013).*
European Application Serial No. 16821921.0, Communication Pursuant to Article 94(3) EPC dated Jan. 31, 2020, 5 pgs.
European Application Serial No. 16821921.0, Communication Pursuant to Article 94(3) EPC dated Jun. 18, 2020, 12 pgs.
European Application Serial No. 16821921.0, Response filed Jun. 4, 2020 to Communication Pursuant to Article 94(3) EPC dated Jan. 31, 2020, 5 pgs.
(Continued)

*Primary Examiner* — Michael Barker
(74) *Attorney, Agent, or Firm* — Schwegman Lundberg & Woessner, P.A.

(57) ABSTRACT

Healthful supplements are described herein. For example, the supplements can include at least four of the following types of nutrients: an amino acid blend, a coconut extract, a vegetable glycerin extract, an alcohol blend, a cannabinoid blend, a hemp plant extract, a *Boswellia serrata* extract, a curcuma/turmeric blend, black cumin seed, an *Artemisia ludoviciana* extract, an *Astragalus* extract, a fenugreek extract, a mushroom extract blend, or any combination thereof.

9 Claims, No Drawings

(56) References Cited

U.S. PATENT DOCUMENTS

2013/0344180 A1 12/2013 Schreuder
2014/0271940 A1 9/2014 Wurzer

FOREIGN PATENT DOCUMENTS

| KR | 20110122961 | 11/2011 |
|---|---|---|
| WO | WO-03021515 A2 | 3/2003 |
| WO | 2014100231 | 6/2014 |
| WO | WO-2017007833 A1 | 1/2017 |
| WO | 2018160702 | 9/2018 |

OTHER PUBLICATIONS

European Application Serial No. 16821921.0, Response filed Dec. 12, 2019 to Extended European Search Report, dated Jun. 4, 2019, 69 pgs.
International Application Serial No. PCT/US2016/041161, International Search Report and Written Opinion dated Nov. 7, 2016, 11 pgs.
International Application Serial No. PCT/US2016/041161, Invitation to Pay Additional Fees and Partial Search Report dated Sep. 7, 2016, 2 pgs.
"International Application Serial No. PCT US2016 041161, International Preliminary Report on Patentability dated Jan. 18, 2018", 9 pgs.
"European Application Serial No. 16821921.0, Partial Supplementary European Search Report dated Feb. 7, 2019", 21 pgs.
"European Application Serial No. 16821921.0, Extended European Search Report dated Jun. 4, 2019", 19 pgs.
"Adult Multi-plus Multi-Vitamins Minerals Purecaps", MINTEL, Database accession No. 2026231, (Mar. 2013), 6 pgs.
"Soymilk Smoothie", MINTEL, Database accession No. 3292183, (Jun. 2015), 3 pgs.
"High protein bar extensions", MINTEL; Database accession No. 10179534, 3 pgs.
"Reishi Shiitake Maitake Mushroom Extract Vegetable Capsules—Solgar Vitamins, Minerals, and Herbs", Solgar Inc., [Online] Retrieved from the internet on May 13, 2019:http: www.solgar.com solgarproducts reishi-shiitake-maitake-mushroom-extract-vegetable-capsules.htm, (May 12, 2015), 1 pg.
Alkaierini, Triantafyllidi, "Herbal and plant therapy in patients with inflammatory bowel disease", Annals of Gastroenterology 28, (2015), 210-220.

* cited by examiner

HEALTHFUL SUPPLEMENTS

CROSS REFERENCE TO RELATED APPLICATIONS

This application is a U.S. National Stage Filing under 35 U.S.C. 371 from International Application No. PCT/US2016/041161, filed on Jul. 6, 2016, and published as WO 2017/007833 A1 on Jan. 12, 2017, which claims the benefit of priority to U.S. Provisional Patent Application Ser. No. 62/189,087 entitled "Healthful Supplements," filed Jul. 6, 2015, the complete disclosure of each of which is incorporated herein by reference in its entirety.

BACKGROUND

Many nutritional supplements and multivitamins are currently available. However, most currently available nutritional supplements fail to provide optimal health benefits. Moreover, currently available nutritional supplements are often developed for mass marketing and consumption. As a result, these nutritional supplements are manufactured to maximize convenience for the consumer and quality is often sacrificed. Mass produced nutritional supplements often include undesirable ingredients such as preservatives, chemicals and heavy metals rather than clean, safe and non-toxic ingredients.

A need therefore exists for clean, safe, and non-toxic dietary nutritional supplements that provide optimal health benefits. Dietary nutritional supplements, such as those described herein, are believed to be particularly useful.

SUMMARY

The supplements described herein have no negative side effects and can optimize health of animals, including humans, who receive them. The supplement contain a number of nutrients including at least four of the following: an amino acid blend, a coconut extract, a vegetable glycerin extract, an alcohol blend, a cannabinoid blend, a hemp plant extract, a *Boswellia serrata* extract, a curcuma/turmeric blend, an *Artemisia ludoviciana* extract, an *Astragalus* extract, a fenugreek extract, a mushroom extract blend, or any combination thereof.

In one example, a supplement contains vegetable glycerin oil; middle chain length triacylglycerols; coconut oil; cannabis root or a hash blend of whole cannabis plant, leaf, flowers, synthetic cannabis oils, or a combination thereof; *Boswellia serrata*; sweet wormwood; fulvic acid minerals/amino acids; turmeric root; and black cumin seed.

The supplements have surprising benefits, such as reducing the incidence and/or severity of disease relative to an animal (or human) who does not receive the supplements. Humans and animals that have received the supplements have reduced pain, disease improvement, more energy, improved sleep patterns, increased activity levels, reduced extremity numbness, improved digestion, fewer headaches, and/or fewer seizures, compared to their own experience prior to taking the supplements.

DETAILED DESCRIPTION

Described herein are supplements that optimize health, and that can reduce the incidence of illness. The supplements contain essential oils, vitamins, minerals, and plant materials. Examples of ingredients in the supplements include vegetable glycerin oil, medium chain triglycerides, fulvic acid, coconut oil, cannabis, turmeric, sweet wormwood, glycine, hemp seeds, black cumin seeds, or combinations thereof. Alternatively, the supplements can contain components of such plant materials such as a blend of amino acid, a coconut extract, vegetable glycerin, a blend of alcohol-containing compounds, a blend of cannabinoids, an extract of hemp plants, a *Boswellia serrata* extract, a curcuma/turmeric blend, an *Artemisia ludoviciana* extract, a mushroom extract blend, and a combination thereof. In some cases the supplements do not contain tetrahydrocannabinol (THC), or the compounds responsible for marijuana's psychological effects. The healthful components of cannabis and the cannabinoids that do not cause the psychological effects of cannabis can be included in all supplement formulations. Thus, when the healthful supplements are routinely administered or ingested (e.g., daily, biweekly, triweekly, weekly and/or via a sustained regimen), the supplements may not contain THC. For example, when the supplements do not contain THC, they can still contain tetrahydrocannabinolic acid (THC-A, the precursor to THC). While being devoid of psycho-activity, THC-A still has many therapeutic benefits, such as aiding in sleep, inhibiting cancer cell growth, and suppressing muscle spasms. The supplements contain pure ingredients, and have a slightly alkaline pH of 7.0 to 7.8. When formulated into a drink or oral formulation, the supplements have a mild taste.

The following provides further information about components in the supplements.

CG Generic Supplement

The CG Generic Supplement contains a mixture of plant materials, fulvic acid, glycine, flavoring and oils. For example, CG Generic Supplement can contain vegetable glycerin, medium chain triglycerides, fulvic acid, coconut oil, cannabis buds containing tetrahydrocannabinol (THC), cannabis leaves containing cannabidiol (CBD), cannabis plant matter (e.g., hash that can include the roots, stalks, buds, leaves, and seeds for acids), cannabis seeds, black cumin seeds (e.g., *Nigella sativa*), turmeric root/plant, sweet wormwood (*Artemisia annua*) whole plant, *Boswellia serrata* whole plant, glycine, hemp seed oil, flavoring (e.g., strawberry flavoring), and combinations thereof.

The supplements can also contain ajulemic acid and/or cp 47, 497-c6-homolog. Ajulemic acid (also called (AB-III-56, HU-239, IP-751, CPL 7075, CT-3, Resunab) is a synthetic cannabinoid derivative of the non-psychoactive THC metabolite, 11nor-9-carboxy-THC. Ajulemic acid has useful analgesic and anti-inflammatory effects without the psychological effects of THC. The structure of ajulemic acid is shown below.

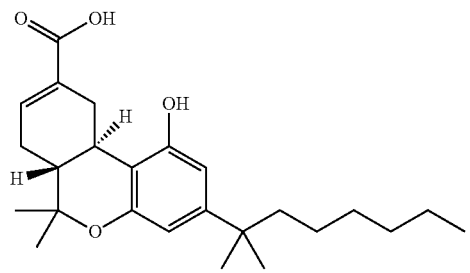 [SMILES: CCCCCCC(C)(C)c1cc(O)c2c(c1)OC(C)(C)[C@@H]1CC=C(C(=O)O)C[C@@H]21]

The cp 47, 497-c6-homolog is an alkylaminoindole (also called cp 47, 497 or cis-5-(1,1 dimethylhexyl)-2-(3-hydroxycyclohexyl)-phenol; CAS Number 70435-06-2 (see website at caymanchem.com). The structure of cp 47, 497-c6 is shown below.

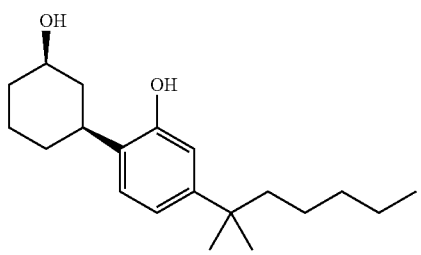 [SMILES: CCCCCC(C)(C)c1ccc([C@H]2CCC[C@@H](O)C2)c(O)c1]

The cp 47, 497-c6 compound has affinity for cannabinoid receptor type 1 (CB1) and peripheral cannabinoid receptor type 2 (CB2). It is a crystalline solid. A stock solution may be made by dissolving the cp 47,497-C6-homolog in the solvent of choice. For example, the cp 47,497-C6-homolog is soluble in organic solvents such as ethanol, methanol, DMSO, and dimethyl formamide (DMF). The solubility of cp 47,497-C6-homolog in ethanol and DMF is approximately 10 mg/ml and approximately 12.5 and 15 mg/ml in methanol and DMSO, respectively. The cp 47,497-C6-homolog is sparingly soluble in aqueous solutions. To enhance aqueous solubility, dilute the organic solvent solution into aqueous buffers or isotonic saline. The solvents can be purged with an inert gas prior to addition of the cp 47,497-C6-homolog. In some cases it is advisable to ensure the residual amount of organic solvent is insignificant, because organic solvents may have physiological effects at low concentrations. It is generally not recommended to store aqueous solutions of cp 47,497-C6-homolog for more than one day. For long term storage, cp 47,497-C6-homolog can be stored in crystalline form at −20° C. It should be stable for at least two years. In general, an individual dose of the CP 47,497-C6-homolog can be about 0.01-40 mg/kg per person. About 1-20 grams of cp 47,497-C6-homolog can be included in the CG Generic Supplement.

The CG Generic Supplement can contain at least four of the components listed in the foregoing paragraph, or at least five of these components, or at least six of these components, or at least seven of these components, or at least nine of these components, or at least ten of these components, or at least eleven of these components, or at least twelve of these components, or all of these components.

In some cases, the CG Generic Supplement contains at least the following ingredients: vegetable glycerin oil; middle chain length triacylglycerols; coconut oil; cannabis root or a hash blend of whole cannabis plant, leaf, flowers, and synthetic cannabis oils; *Boswellia serrata*; sweet wormwood; fulvic acid minerals/amino acids; turmeric root; and black cumin seeds.

To prepare the CG Generic Supplement, the plant materials and seeds can be dried and ground up to form a particulate preparation or powder. Although there are several ways to prepare the CG Generic Supplement, the following is an example of a useful preparation procedure. The amounts or portions of the listed ingredients can be varied and a decision to vary the amounts or portions is within the ken of those of skill in the art.

The oils can generally be mixed together first to form a mixture referred to as "Part 1," which can act as a solvent or medium to support and homogenize the other components. The Part 1 oils also help release useful compounds from the plant materials with which the Part 1 oils are later mixed. Thus, Part 1 can contain glycerin (4 parts), medium chain triglycerides (1 part), coconut oil (1 part), and/or hemp seed oil (2 parts). When all four oils are combined, the ratio of the oils can be: glycerin (4 parts), medium chain triglycerides (1 part), coconut oil (1 part), and hemp seed oil (2 parts).

A portion of the Part 1 mixture of oils (e.g., half) can then be mixed with the ground up cannabis buds and cannabis seeds using mild heat (e.g., up to 47-48° C.) to help release useful compounds from the cannabis materials. This mixture of oils and cannabis buds and seeds is referred to as Part 2. Part 2 can contain 96 times more of the Part 1 oils than of the cannabis seeds, and a volume of cannabis buds that is about one-sixth of the volume of the part 1 oils.

Part 3 is formed by mixing a portion (e.g., half) of the Part 1 oils with cannabis leaves and cannabis seeds using mild heat (e.g., up to 47-48° C.) to help release useful compounds from the cannabis materials. Part 3 can contain 96 times more of the Part 1 oils than of the cannabis seeds, and a volume of cannabis leaves that is about one-sixth of the volume of the part 1 oils.

Part 4 is formed by mixing about 4 parts fulvic acid with 1 part cannabis matter (e.g., for acids), and then centrifuging the mixture using a cold centrifuge (about 4° C.) to remove debris (300-1200 rpm).

Part 5 is formed by mixing together about 110 parts coconut oil, about 1 part flavoring (e.g., strawberry flavoring), about 1 part cannabis buds, about 1 part cannabis leaves, about 0.25 part cannabis seeds, about 8 parts glycine, about 20 parts turmeric root/plant, about 10-40 parts black cumin seed, about 28 parts sweet wormwood, and about 20 parts *Boswellia serrata*. While mixing well, the Part 5 materials can be mildly heated (e.g., up to 47-48° C.) to help release useful compounds into the mixture.

Then each of the Parts listed above are mixed together.

For example, to form Part 6, Part 2 is mixed with Part 3, and the combination is centrifuged using a cold centrifuge (about 4° C.) to remove debris (300-1200 rpm).

Part 7 is formed by mixing Part 6 with Part 4, and the combination is centrifuged using a cold centrifuge (about 4° C.) to remove debris (300-1200 rpm).

Part 8 is the final mixture, which is formed by mixing Part 7 with Part 5 and then centrifuging mixture using a cold centrifuge (about 4° C.) to remove debris (300-1200 rpm). Hence, Part 8 is the CG Generic Supplement.

Although the CG Generic Supplement is useful as a healthful dietary supplement, the CG Medlife Supplement appears to provide even more benefits. The CG Medlife Supplement contains many individual compounds, and the ratios of these compounds can be varied to enhance the benefits of the CG Medlife Supplement.

CG Medlife Supplement

The CG Medlife Supplement can contain a number of nutrients including an amino acid blend, a coconut extract, a vegetable glycerin extract, an alcohol blend, a cannabinoid blend, a hemp plant extract, a *Boswellia serrata* extract, a curcuma/turmeric blend, an *Artemisia ludoviciana* extract, an *Astragalus* extract, a fenugreek extract, a mushroom extract blend, or any combination thereof. The supplements can also contain Indian gooseberry, green cardamom, black cardamom, spinach (e.g., *Spinacia oleracea*), black cumin seeds (e.g., *Nigella sativa*), pumpkin seed powder, pepper (e.g., *Piper nigrum*), Guinea hen weed root, Prickly pear fruit, ajulemic acid, and/or cp 47, 497-c6-homolog.

The CG Medlife Supplement can contain at least four of these components, or at least five of these components, or at least six of these components, or at least seven of these components, or at least eight of these components, or at least nine of these components, or at least ten of these components, or at least eleven of these components, or at least twelve of these components, or at least thirteen of these components, or at least fourteen of these components, or all of these components. The CG Medlife Supplement is 100% pure, with a slightly alkaline pH of 7.0 to 7.8. It has a mild taste.

The composition of the Sports Drink or Preventative Supplement is similar to the CG Medlife Supplement, but the Sports Drink/Preventative Supplement does not contain psychoactive cannabinoids such as THC. In addition, some of the ingredients in the CG Medlife Supplement may not be included in the Sports Drink/Preventative Supplement, and vice versa.

Components that can be included in the CG Medlife Supplement and the Sports Drink/Preventative Supplement are further described below.

Amino Acid Blend

The amino acid blend of the CG Medlife Supplement and the Sports Drink/Preventative Supplement can include alanine, arginine, aspartic acid, cysteine, cystine, glutamic acid, glycine, histidine, isoleucine, lysine, leucine, methionine, phenylalanine, serine, proline, threonine, tryptophan, tyrosine, valine, fulvic-humic acids, and combinations thereof. For example, amino acid blend of the CG Medlife Supplement and the Sports Drink/Preventative Supplement can contain at least four of these amino acids, or at least five of these amino acids, or at least six of these amino acids, or at least seven of these amino acids, or at least nine of these amino acids, or at least ten of these amino acids, or at least twelve of these amino acids, or at least fourteen of these amino acids, or at least fifteen of these amino acids, or at least seventeen of these amino acids, or at least eighteen of these amino acids, or all of these amino acids.

The amino acid blend of the CG Medlife Supplement and the Sports Drink/Preventative Supplement can also include small amounts of minerals or salts thereof, such as antimony, barium, beryllium, bismuth, boron, bromine, cadmium, calcium, cerium, cesium, chloride, chromium, cobalt, copper, dysprosium, erbium, europium, fluorine, gadolinium, gallium, germanium, gold, hafnium, holmium, indium, iodine, iridium, iron, lanthanum, lithium, lutetium, magnesium, manganese, molybdenum, neodymium, nickel, niobium, osmium, palladium, phosphorous, platinum, potassium, praseodymium, rhenium, rhodium, rubidium, ruthenium, samarium, scandium, selenium, silicon, silver, sodium, strontium, sulfur, tantalum, tellurium, terbium, thulium, thorium, tin, titanium, tungsten, vanadium, ytterbium, yttrium, zinc, zirconium, or any combination thereof. The minerals the listed elements can be used as salts. For example, the listed elements can be employed as their customary cations and/or anions in combination with corresponding gegenions. For cations, the halogen, sulfate, nitrate, and phosphate salts are typically employed. For anions such as oxygenated forms of transition metals and non-metallic elements (Groups III-VII of the Periodic Chart), alkaline and alkaline earth metal salts are typically employed.

A convenient source of the fulvic-humic acids and the minerals used in the supplements described herein is Vital Earth—Fulvic Mineral Complex Ionic Mineral Supplement (see. e.g., website at vitacost.com/vital-earth-minerals-fulvic-mineral-complex?csrc=GPF-PA-Vitamins%20%26%20Supplements-855748000016&ci_gpa=pla&ci_kw=&ci_src=17588969&ci_sku=855748000016&C Glid=CM6DquuutcYCFdgLgQodpK0MFQ). One serving of Vital Earth—Fulvic Mineral Complex Ionic Mineral Supplement can be about 0.5 to about 2 fluid ounces.

For a single serving, the amount of each component of the amino acid blend can range from about 0.1 mg/Kg to about 50 mg/Kg, or from about 0.5 mg/Kg to about 30 mg/Kg, or from about 1 mg/Kg to about 25 mg/Kg.

Fulvic Acid/Humic Acid

Humic acid is a component of humic substances, which are the major organic constituents of soil (humus), peat, coal, many upland streams, dystrophic lakes, and ocean water. Humic acid is produced by biodegradation of dead organic matter. It is not a single acid. Instead, it is a complex mixture of many different acids containing carboxyl and phenolate groups so that the mixture behaves functionally as a dibasic acid or, occasionally, as a tribasic acid. Humic acids can form complexes with ions that are commonly found in the environment creating humic colloids. Fulvic acids are humic acids of lower molecular weight and higher oxygen content than other humic acids.

Humic substances in soils and sediments can be divided into three main fractions: humic acids, fulvic acids, and humin. The humic and fulvic acids can be extracted as a colloidal sol from soil and other solid phase sources using basic aqueous solutions of sodium hydroxide or potassium hydroxide. Humin is insoluble in dilute alkali and is therefore not collected by basic extraction. Humic acids are precipitated from basic solutions by adjusting the pH to 1 with hydrochloric acid, leaving the fulvic acids in solution. This solubility difference at acidic pH is the operational distinction between humic and fulvic acids.

Humic and fulvic acids are commonly used as a soil supplement in agriculture, and less commonly as a human nutritional supplement. As a nutrition supplement, fulvic acid can be found in a liquid form as a component of mineral colloids. Fulvic acids are poly-electrolytes and are unique colloids that diffuse easily through membranes whereas all other colloids do not.

Humic and fulvic acids can react with the chemicals used in the chlorination process, which is sometimes used for generating drinking water, to form disinfection byproducts such as dihaloacetonitriles, which are toxic to humans. Although water is generally not used for preparing humic and fulvic acids or the supplements described herein, if water is used to prepare or formulate humic and fulvic acids, a pure source of water (without chlorine or chlorination byproducts) is used.

The amount of humic/fulvic acids that are present in a single serving of the amino acid blend part of the CG Medlife Supplement and the Sports Drink/Preventative Supplement can range from about 1 mg/Kg to about 50 mg/Kg, or from about 5 mg/Kg to about 40 mg/Kg, or from about 10 mg/Kg to about 30 mg/Kg. In many cases humic/fulvic acid content can be about 20 mg/Kg per serving.

Humic and fulvic acids are available commercially and can be obtained, for example, from SupremeFulvic (see website at SupremeFulvic.com).

Coconut Extract

Whole mature coconut is used for making the components of the supplements described herein. For example, the meat and milk of whole coconut(s) can up ground up to release useful liquid components such as coconut oil, middle chain-length triacylglycerols (MCT) such as caprylic acid, and other useful components. After grinding to generate slurry, the slurry can be heated up to 65° C. to release the MCT. Some of the properties of these middle chain-length triacylglycerols are shown below.

| | MCT |
|---|---|
| Melting point | 65° C. |
| Boiling point | 251° C. |
| logP | 1.37 |

Human serum albumin (HSA) can bind MCT (e.g., caprylic acid), and such binding can be an indicator of the purity and/or physiological benefits of the MCT. Lyophilized HSA powder (fatty acid free, ≥99%) can be purchased from Sigma. A 50 mg/mL HSA solution can be prepared in 1× phosphate buffered saline (PBS) and spiked with caprylic acid as a control to illustrate the binding properties of HSA. A known volume of an MCT preparation (such as that prepared from coconut) can be added to a second aliquot of 50 mg/mL HSA solution in PBS. The HSA protein can be separated from the unbound MCTs (and caprylic acid) using mild separation procedures such as gel chromatography. Caprylic acid in the control, and the other MCTs from a test sample, can be extracted from the HSA by adding a two-fold sample volume of 0.04% trifluoroacetic acid (TFA) in acetonitrile to the sample. The sample can then be vortexed briefly and centrifuged to remove the precipitated protein. The supernatants containing caprylic acid or MCT can be analyzed by HPLC to determine its purity and concentration (mg/mL).

The amount of caprylic acids, MCT, and coconut present in a single serving of the CG Medlife Supplement and the Sports Drink/Preventative Supplement can vary. For example, the caprylic acid content can range from about 1 mg/Kg to about 40 mg/Kg, or from about 5 mg/Kg to about 30 mg/Kg, or from about 10 mg/Kg to about 25 mg/Kg. In many cases the caprylic acid from the coconut preparation can be about 15 mg/Kg per serving. The MCT content can range from about 5 mg/Kg to about 60 mg/Kg, or from about 10 mg/Kg to about 50 mg/Kg, or from about 15 mg/Kg to about 40 mg/Kg. In many cases the MCT within the coconut preparation can be about 25 mg/Kg per serving. The coconut oil content can range from about 10 mg/Kg to about 100 mg/Kg, or from about 20 mg/Kg to about 80 mg/Kg, or from about 25 mg/Kg to about 60 mg/Kg per serving. In many cases the coconut oil within the coconut preparation that is used in the CG Medlife Supplement and the Sports Drink/Preventative Supplement can be about 40 mg/Kg per serving.

Vegetable Glycerin

Vegetable glycerin, or glycerol, is a clear, odorless liquid produced from plant oils. For example, the vegetable glycerin can be obtained from palm oil, soy oil, coconut oil, or a combination thereof. It has a flash point of approximately 177° C., and a boiling point of 290° C. (554° F.). Accordingly, it can be subjected to processing at room temperature and at the temperatures described herein for manufacturing the supplement. Vegetable glycerin is relatively nontoxic. The MSDS indicates that the $LD_{50}$ oral rat dosage is 12,600 milligrams per kilogram of body weight, which is approximately 5.7 grams per pound of body weight, or 36 ounces for a 180 pound male. By comparison, acute oral toxicity ($LD_{50}$) in rats for sucrose (table sugar) is 29700 mg/kg and the acute oral toxicity ($LD_{50}$) in rats for ethyl (grain) alcohol is about 7060 mg/kg. At saturation, glycerin only hold as 33% as much cannabis oil as the same volume of ethyl (grain) alcohol, so about three times more glycerin is used per dose than would be used if ethyl alcohol were uses as a solvent for cannabis oil. Vegetable glycerin can be obtained from a variety of sources such as from Bulk Apothecary (see website at bulkapothecary.com/raw-ingredients/other-ingredients-and-chemicals/glycerin/?gclid=CIabgs_2pcYCFUI8gQodcmYNHw) or from Sigma-Aldrich (see website at sigmaaldrich.com/catalog/search?term=Glycerine&interface=All&N=0&mode=partialmax&lang=en&region=US&focus=product).

The amount of glycerin that are present in a single serving of the CG Medlife Supplement and the Sports Drink/Preventative Supplement can range from about 5 mg/Kg to about 100 mg/Kg, or from about 10 mg/Kg to about 80 mg/Kg, or from about 20 mg/Kg to about 60 mg/Kg. In many cases the glycerin content can be about 45 mg/Kg per serving.

Alcohol Blend

The Alcohol Blend described herein is a mix of compounds that not only contain alcohol (hydroxy) moieties but also terpenes and terpene-like compounds. The Alcohol Blend can contain compounds such as alpha-humulene, alpha-phellandrene, alpha-pinene, alpha-terpinene, alpha-terpinolene, beta-myrcene, beta-pinene, camphene, cis-ocimene, delta-3-carene, limonene, linalool, pulegone, sabinene, trans-caryophyllene, trans-ocimene, gamma-terpinene, α-terpincol, terpineol-4-ol, 1.8-cineole, perillyl alcohol, p-cymene, and combinations thereof. For example, the Alcohol Blend can contain at least four of these compounds, or at least five of these compounds, or at least six of these compounds, or at least seven of these compounds, or at least nine of these compounds, or at least ten of these compounds, or at least twelve of these compounds, or at least fifteen of these compounds, or at least seventeen of these compounds, or at least nineteen of these compounds, or all of these compounds. In some cases, one or more of the compounds listed above are not present in the Alcohol Blead. For example, in some cases p-cymene is not included in the Alcohol Blend. Further information on some of the compounds that can be present in the Alcohol Blend is provided below.

β-myrcene Boiling point: 166-168° C.; Properties: Analgesic. Anti-inflammatory, Antibiotic, Anti-mutagenic;

β-caryophyllene Boiling point: 119° C.; Properties: Anti-inflammatory, Cytoprotective (gastric mucosa), Antimalarial;

d-limonene Boiling point: 177° C.; Properties: Cannabinoid agonist, Immune potentiator, Antidepressant, Anti-mutagenic;

linalool Boiling point: 198° C.; Properties: Sedative, Antidepressant, Anxiolytic, Immune potentiator;

pulegone Boiling point: 224° C.; Properties: Memory booster, AChE inhibitor, Sedative, Antipyretic;

1,8-cineole (eucalyptol) Boiling point: 176° C.; Properties: AChE inhibitor, Increases cerebral, blood flow, Stimulant, Antibiotic, Antiviral, Anti-inflammatory, Anti-nociceptive;

α-pinene Boiling point: 156° C.; Properties: Anti-inflammatory, Bronchodilator, Stimulant, Antibiotic, Antineoplastic, AChE inhibitor;

α-terpineol Boiling point: 217-218° C.; Properties: Sedative, Antibiotic, AChE inhibitor, Antioxidant, Antimalarial terpineol-4-ol Boiling point: 209° C.; Properties: AChE inhibitor. Antibiotic p-cymene Boiling point: 177° C.; Properties: Antibiotic, Anti-candida. AChE inhibitor The amounts of alpha-humulene, alpha-phellandrene, alpha-pinene, alpha-terpinene, alpha-terpinolene, beta-myrcene, beta-pinene, camphene, cis-ocimene, delta-3-carene, limonene, linalool, pulegone, sabinene, trans-caryophyllene, trans-ocimene, gamma-terpinene, α-terpineol, terpineol-4-ol, 1.8-cineole, perillyl alcohol, and p-cymene within the Alcohol Blend can vary. For example, the amounts of each of these components can range from about 0.01 mg/Kg to about 60 mg/Kg, or from about 0.05 mg/Kg to about 50 mg/Kg. or from about 0.1 mg/Kg to about 40 mg/Kg per serving.

Perillyl Alcohol

Perillyl alcohol and its precursor limonene are monocyclic terpenes derived from the mevalonate pathway in plants. Perillyl alcohol can be found in the essential oils of various botanicals, such as lavender, lemongrass, sage, and peppermint. Perillyl alcohol is abundant in fruits such as oranges. For example, perillyl alcohol can be obtained from Korean orange peel using supercritical fluid extraction (SFE). The fluid commonly employed for SFE is carbon dioxide. For example, perillyl alcohol can be obtained from Korean orange peel using $CO_2$ at operating conditions of 50° C., 200 bar, and 6 $CO_2$ kg/h/kg sample. Most of the perillyl alcohol can be extracted within 14 hours using such a technique. The yield of extract containing perillyl alcohol can be about 2.5% based on the dry powder of the orange peel. The content of perillyl alcohol in the orange peel was $2.8 \times 10^{-3}$ (wt %) by GC analysis based on the dry powder, which indicated that SFE was approximately 30 times more efficient than previously reported solvent-extraction methods. The SFE extracts can be further purified by open tubular chromatography. HPLC can also be used to identify fractions containing perillyl alcohol in extracts.

Perillyl alcohol can be part of the Alcohol Blend described herein. The amount of perillyl alcohol in the supplements can vary. For example, the amounts of perillyl alcohol can range from about 0.01 mg/Kg to about 10 mg/Kg, or from about 0.05 mg/Kg to about 5 mg/Kg, or from about 0.1 mg/Kg to about 2 mg/Kg per serving. In many cases, the amount of perillyl alcohol can be about 1 mg/Kg per serving.

Limonene

Limonene is a colorless liquid hydrocarbon classified as a cyclic terpene. Limonene can be obtained from orange peels. For example, to obtain limonene, the outer orange-colored rind of two oranges can be grated and added to 100 ml of distilled water in a 250 ml round bottomed flask for distillation. Heat the flask so that distillation proceeds at a steady rate, approximately one drop per second of distillate. (Note: Take care not to let the liquid in the round bottomed flask boil too strongly). The distillate can be collected in a measuring cylinder to facilitate removal of the oil layer, which will be the top layer. Limonene can be detected using bromine water because only unsaturated (C=C) double bond hydrocarbons decolorize bromine. For example, to detect limonene, approximately 1 ml of bromine water can be placed into each of three test tubes. Add a few drops of the sample suspected of containing limonene oil to one test tube, a few drops of cyclohexane to another (negative control), and a few drops of cyclohexene (positive control) to a third tube. Agitate the tubes. If the bromine water is decolorized, the sample contains a molecule with double bonds. 0.001M potassium manganate(VII) can be substituted for the bromine water.

The amount of limonene in the Alcohol Blend can vary. For example, the amounts of limonene can range from about 1 mg/Kg to about 60 mg/Kg, or from about 5 mg/Kg to about 50 mg/Kg, or from about 10 mg/Kg to about 40 mg/Kg per serving. In many cases, the amount of limonene can be about 30 mg/Kg per serving.

Beta-Myrcene

If released into air at about 25° C., myrcene will exist solely as a vapor in the atmosphere. Vapor-phase myrcene will also be degraded in the atmosphere by reaction with photochemically-produced hydroxyl radicals, ozone and nitrate radicals. The half-lives for these reactions in air are estimated to be 1.8 hours, 34 minutes and 4 minutes, respectively. Hydroxyl radical and ozone oxidation of myrcene in the ambient atmosphere yields acetone, formaldehyde and formic acid as degradation products. Myrcene does not contain chromophores that absorb at wavelengths greater than 290 nm. Hence, to retain beta-myrcene within the supplements it is advisable to maintain the Alcohol Blend and the final supplement formulation in sealed containers to prevent oxidation and loss of beta-myrcene to the atmosphere.

The amount of beta-myrcene in the Alcohol Blend can vary. For example, the amounts of beta-myrcene can range from about 0.01 mg/Kg to about 10 mg/Kg, or from about 0.05 mg/Kg to about 5 mg/Kg, or from about 0.1 mg/Kg to about 2 mg/Kg per serving. In many cases, the amount of beta-myrcene can be about 0.7 mg/Kg per serving.

Cannabinoids

Cannabinoids can be obtained from *Cannabis sativa* (e.g., Thailand Sative) and/or *Cannabis indica* (e.g. *Indica*). A variety of cannabinoids can be employed in the formulations described herein. For example, the cannabinoids employed in the CG Medlife Supplement and the Sports Drink/Preventative Supplement can include 9-tetrahydrocannabinol (THC), tetrahydrocannabinolic acid (THC-A), cannabidiol (CBD), cannabidiolic acid (CBDA), cannabigerol (CBG), cannabichromene (CBC), cannabinol (CBN), whole cannabis plants, and combinations thereof. In some instances, the supplements contain ajulemic acid and/or cp 47, 497-c6-homolog. Ajulemic acid is a synthetic cannabinoid derivative of the non-psychoactive THC metabolite 11-nor-9-carboxy-THC. Ajulemic acid has useful analgesic and anti-inflammatory properties without causing psychological effects. The cp 47, 497-c6 compound is a cannabinoid receptor agonist.

The supplements can contain at least two of these cannabinoid compounds, or at least three of these cannabinoid compounds, or at least four of these cannabinoid compounds, or at least five of these cannabinoid compounds, or at least six of these cannabinoid compounds, or at least seven of these compounds, or at least eight of these compounds. In some cases, the supplements contain all of these compounds. However, in some cases, one or more of the compounds listed above are not present in the supplements. For example, a Sports Drink/Preventative supplement described herein does not contain added THC.

Some of the properties of cannabinoids that can be included in the formulations are described below.

9-tetrahydrocannabinol (THC) Boiling point: 157° C.; Properties: Euphoriant, Analgesic, Anti-inflammatory, Antioxidant, Antiemetic;

cannabidiol (CBD) Boiling point: 160-180° C./320-356 degree Fahrenheit Properties: Anxiolytic, Analgesic, Antipsychotic, Anti-inflammatory, Antioxidant, Antispasmodic;

cannabinol (CBN) Boiling point: 185° C.; Properties: Oxidation, breakdown, product, Sedative, Antibiotic;

cannabichromene (CBC) Boiling point: 220° C.; Properties: Anti-inflammatory, Antibiotic, Antifungal;

cannabigerol (CBG) Boiling point: 52° C.; Properties: Anti-inflammatory. Antibiotic, Antifungal;

δ-8-tetrahydrocannabinol (δ-8-THC) Boiling point: 175-178° C.; Properties: Resembles δ-9-THC, Less psychoactive, More stable Antiemetic;

tetrahydrocannabivarin (THCV) Boiling point: <220° C.; Properties: Analgesic, Euphoriant;

ajulemic acid (Resunab) Molecular weight 400.55; melting point 96 to 99° C. analgesic and anti-inflammatory Biopathway delta 8 through 11 dosage about 1 mg/kg cp 47,497-C6( ) Also known as 2-[(1S,3R)-3-hydroxycyclohexyl]-5-(1,1-dimethylhexyl)phenol. Molecular weight 304.47 g/mol; individual dose 0.01-40 mg/kg per person and combinations thereof.

Useful compounds can be obtained from cannabis by a variety of procedures. The following provides information on processing cannabis, for example, to obtain useful compounds.

A glass-filter (mesh size 2) of about 5 cm in diameter and 7 cm in height is two-thirds filled with acid-washed sea-sand (Sigma) and topped with glass pearls (±1 mm diameter). Before use, the sand is sequentially washed with 200 ml of hexane, ethanol and water. *Cannabis* extracted with hexane is concentrated into about 5 ml of hexane, placed drop-wise on top of the sand filter, and evaporated by using a warm air blower. The sand filter is then placed onto a suction Erlenmeyer and acidic cannabinoids are eluted by washing the sand filter under vacuum with a 0.1 M NaOH solution. The elution is continued until the eluate turns from deep-orange to colorless. Neutral cannabinoids and other compounds can then be eluted with ethanol (200 ml), followed by hexane (200 ml).

Acidic cannabinoids can be precipitated in the aqueous eluate by adding HCl until the pH reaches about pH 2, and then by filtering through the (dried) sand filter. The precipitate that remained on top of the sand filter can then be eluted with ethanol (200 ml).

The acidic cannabinoids fraction, resulting from the sand filter separation, is the preferred starting material for the isolation of cannabinoids, because it is free of interfering compounds such as lipids or terpenoids, and it contains the highest yield of extracted cannabinoids. About ⅔ of the weight of the total hexane extract can be recovered in the acidic cannabinoids fraction.

Ideally, cannabis is dried before it is extracted. In general, it may not possible to remove more than 50% of the cannabinoids from fresh material (e.g., THC-Acid is difficult to extract). If you plan to convert the THCA to THC, the plant material it is advisable to thoroughly decarboxylate the plant material by heating it under nitrogen at 105° C. for 1 hour before performing a solvent extraction.

Chloroform is the most efficient solvent for the extraction of THC from cannabis. A single extraction will remove 98-99% of the cannabinoids within 30 minutes. A second extraction removes only 88-99% of the remaining cannabinoids within 30 minutes but such a second extraction removes 100% of the THC. Light petroleum ether (60-80° F. or 15.5° C.-26.6° C.) also works well, but a single extraction removes only 88-95% of the cannabinoids; a second extraction removes up to 99% of the cannabinoids. Ethanol also can be used, but it removes ballast pigments and sugars that can complicate further purification.

The dried cannabis can be extracted with a suitable solvent for several hours at room temperature or by refluxing. The extract can be filtered through charcoal to clarify the solution. Waxes can be removed by chilling the extract overnight, which precipitates the waxes. After wax precipitation, the extract solution can be filtered and concentrated to about one-half of its volume. The concentrate can then be extracted with 2% aqueous sodium sulfate (to prevent oxidation). When the aqueous layer is removed and the solvent is stripped away, the residue is crude hemp oil.

The odoriferous terpenes can be removed by steam or vacuum distillation. Note that cautious distillation in vacuo yields a fraction of crude red oil (boiling point 100-220° C./3 mm). This oil can be purified by redistillation or column chromatography. Ethanol can be used to remove the residue from the flask while it is still hot. The solution can be filtered through charcoal. The solvent can be removed to yield a residue. When the residue is subjected to distillation, a pure red oil is generated (boiling point 175-195° C./2 mm).

Because THC is heat-sensitive, it is preferable to isolate the cannabinoids by column chromatography. The simplest method of column chromatography is performed with ethanol and ether extracts of hemp on alumina, yielding two major fractions: (1) chlorophyll, CBD, and CBN, and (2) THC. A second, more difficult method is performed on Florisil® (use 10 times the weight of the oil) with the solvent system being hexane: 2% methanol. This yields a concentrated viscous oil that can be repeatedly chromatographed on alumina to separate the THC and CBD.

The amounts of 9-tetrahydrocannabinol (THC), tetrahydrocannabinolic acid (THC-A), cannabidiol (CBD), cannabidiolic acid (CBDA), cannabigerol (CBG), cannabichromene (CBC), cannabinol (CBN), ajulemic acid, and whole cannabis plant materials within the CG Medlife Supplement and the Sports Drink/Preventative Supplement can vary. For example, the amounts of each of these components in a single serving can range from about 1 mg/Kg to about 2000 mg/Kg, or from about 2 mg/Kg to about 1500 mg/Kg, or from about 2 mg/Kg to about 1200 mg/Kg. In general, the amount of whole cannabis in the supplements is larger than the pure cannabinoids. For example, the amount of whole cannabis plant material in a single serving of the supplements can range from about 100 mg/Kg to about 2000 mg/Kg, or from about 400 mg/Kg to about 1500 mg/Kg. For example, in many cases the amount of whole cannabis plant material per serving can be about 1000 mg/Kg. The cannabinoid compounds, including Ajulemic acid, can be provided in lower amounts such as from about 1 mg/Kg to about 10 mg/Kg per serving.

The cp 47,497-C6-homolog can be added to the cannabinoid mixture. In general, an individual dose of the cp 47,497-C6-homolog can be about 0.01-40 mg/kg per person. About 1-20 grams of cp 47,497-C6-homolog can be included in the Medlife Supplement.

Preparation and Materials for Making Plant Hash Using Carbon Dioxide (Dry Ice)

When preparing extractions with $CO_2$, high quality materials are used for best possible results. For example, high grade materials are available from CG Bio Genomics. The following process is useful for extraction of cannabis plant material. For example, trichome glands from cannabis plant material can be recovered by the following process.

The extraction process can employ Ice-o-Lator extraction bags (see, e.g., website at pollinator.nl/default_center.asp?link_id=10&category_id=19 or pollinator.nl/default_center.asp?link_id=11 &category_id=19&sub_category_id=105) or similar bags. A 120 to 160 micron bag can be employed initially, and the screen size can be gradually reduced according to the trichome size and concentration desired.

There are different types and sizes of trichome glands. The morphology of these glands can depend on plant genetics. For example, trichome glands can range from up to about 160 microns or more, while others measure even less than 25-50 microns. For the processes described herein, glands measuring from about 25 to 200 microns, or from about 50 to 150 microns, or from about 70 to 120 microns. Glands of about 70 to 120 microns generally yield the best quality. If the screens are smaller than the collected glands, the dry sift extraction will also be smaller.

Another factor to consider is the dry ice or the solid form of carbon dioxide, and how the dry ice is used for cannabis resin extractions. To perform the extraction, a first step can involve storage and removal of the cannabis plant material from a freezer. *Cannabis* plant matter releases the resin glands more easily and more quickly when in contact with the dry ice than when the plant material is at room temperature. If cannabis buds are large and compact, they may need to be crumbled into smaller buds to increase the plant surface in contact with the dry ice. A second step can involve mixing the cannabis plant material with the dry ice in a container made of a non-toxic material where the container does not degrade with cold temperatures. The plant material can be gently mixed. The plant material (e.g., 20-30 grams) can then be poured into a 120-160 micron Ice-o-Lator or Cristalizer hash extraction mesh and gently sieved for no more than 15-20 second onto a smooth and clean surface prepared (PTFE film). For example, with the dry ice and the plant material (e.g., buds) inside the Ice-O-Lator bag, the Ice-o-Lator or Cristalizer sieve bag can be shaken gently and slowly for a few seconds. More dry ice can be added, mixed, with gentle sieving of plant material to recover more resin.

Such a process can provide top grade plant hashish.

Indian Gooseberry

Indian gooseberry, for example, *Emblica officinalis* (of the family Euphorbiaceae) is also known as *Amla* or *Amla churna* (the latter referring to the dried fruits). Indian gooseberry is a component of some Ayurveda combination therapies such as Chyawanprash and Triphala. This plant is also known as *Phyllanthus emblica* and *Amla* is sometimes used interchangeably with Anwala, Amlaj, or Amlaki.

The fruits are traditionally used in Egypt for improving memory, as a stimulant, and as a restorative for all organs. Indian gooseberry can be used for the treatment or prevention of diarrhea, jaundice, inflammation, cerebral insufficiency, and mental disorders. In some cases, Indian gooseberry can be used as an appetite stimulant or for the treatment of diabetes. Among some ayurvedic texts (Charaka Samhita and Sushruta Samhita), this herb is referred to as the "best among the sour fruits" or "the best among rejuvenative herbs". As suitable dosage can be 50-200 mg/kg for oral ingestion of the fruit.

The Indian gooseberry fruit (e.g., kg fresh fruit) can be washed with clean water. The gooseberries can be cut into small pieces and the seeds removed. Such small pieces can be ground or mixed to make a paste. The paste can be placed in a clean double folded cotton cloth, the cloth can be wrapped around the fruit paste and squeezed tightly to extract the juice. The pulp can be retained in a convenient container. This procedure can be repeated with any remaining fruit pieces. The yield can be approximately 600 grams of juice from 1 kg amla.

Green and/or Black Cardamom

Green cardamom (*Elettaria cardamomum* (L.) Maton var, cardamomum Plant Family: Zingiberaceae) and/or black cardamom (*Amomum costatum* and *Amomum subulatum*) can be employed in the supplements.

The sweetly aromatic cardamom is the fruit of a tropical plant related to ginger, and is one of the world's most expensive spices, after saffron and vanilla. Growing cardamom is extremely labor intensive. The tall plants, grown on plantations in Guatemala or India, flower for eight or nine months of the year. Each pod, or capsule, ripens slowly, and must be plucked when it is three-quarters ripe.

Cardamom is used in cuisines of the Middle East and Scandinavia. Cardamom coffee or gahwa is a symbol of Arab hospitality. Cardamom flavors ground meat in Norway and baked goods in Sweden. Cooks all over the world combine cardamom with cloves and cinnamon. Cardamom lends its distinctive flavor to chai.

After harvest, the pods are washed and dried. The method of drying dictates the final color. White indicates the pods have been dried for many days in the sun leaving them bleached. Green pods can be dried for one day and night in a heated room. The three seeds inside each pod are considered to be the spice. The seeds can be ground up, including the papery pods, to yield a fine powder. The amount of cardamom used in the CG Medlife Supplement and/or the Sports Drink/Preventative Supplement can be about 1 g/10 mL to about 1 g/Kg. For example, subjects can be administered up to about 0.1 g to about 10 g daily, or about 0.5 g to about 5 g daily, or about 1 g to 3 g daily.

Spinach

Powders or aqueous extracts of spinach (e.g., *Spinacia oleracea* L. Plant Family: Chenopodiaceae) can be included in the CG Medlife Supplement and/or the Sports Drink/Preventative Supplement described herein.

For example, the amount of black seed extract per single serving can range from about 0.1 mg/Kg to about 80 mg/Kg, or from about 0.5 mg/Kg to about 44 mg/Kg, or from about 1 mg/Kg to about 80 mg/Kg. In many cases, the amount of *Spinacia oleracea* can be about 60 mg/Kg per serving.

One method of preparing useful components from these plants involves grinding of dried *Spinacia oleracea* (e.g., 500 g) followed by separation through a vibrating sieving machine. Four different particle sizes can be separated: the 60 mesh (about 250 μm and smaller) size, 44 mesh (about 350 μm and small) size, 30 mesh (about 595 μm and smaller) size and above 30 mesh (about 595 μm and larger) size. The powders can be accumulated and then sealed separately with labeling for further analysis and processing.

In some cases, fresh or dried spinach can be ground, and 30 grams can be boiled per liter water for 10-30 minutes to provide a suspension that can be employed in the supplements. Spinach is generally recognized as safe at a variety of ingested amounts. Hence, he amount of spinach used in the CG Medlife Supplement and/or the Sports Drink/Preventative Supplement can vary.

Flavonoid and Phytosterol Components

*Cannabis* can also contain flavonoids and phytosterols. Examples of some of the flavonoids and phytosterols that can be present in cannabis include any of the following.

apigenin Boiling point: 178° C.; Properties: Anxiolytic, Anti-inflammatory, Estrogenic quercetin Boiling point: 250° C.; Properties: Antioxidant, Anti-mutagenic, Antiviral. Antineoplastic cannflavin A Boiling point: 182° C.; Properties: COX inhibitor, LO inhibitor β-sitosterol Boiling point: 134° C.; Properties: Anti-inflammatory, 5-a-reductase, inhibitor Hemp Oil The CG Medlife supplement can include a variety of oils from hemp. These hemp oil is preferably obtained by cold-pressing hemp. Cold pressed, unrefined hemp oil is dark to clear light green in color, with a nutty flavor. The darker the color, the grassier the flavor of hemp oil. Hemp oil has high nutritional value because it contains essential fatty acids in useful ratios, for example, a 3:1 ratio of omega-6 to omega-3 essential fatty acids. Hemp oil can also contain omega-9 fatty acids.

Omega-6 fatty acids (also referred to as ω-6 fatty acids or n-6 fatty acids) are a family of pro-inflammatory and anti-inflammatory polyunsaturated fatty acids that have a final carbon-carbon double bond in the n-6 position, that is, the sixth bond, counting from the methyl end. Omega-3 fatty acids are polyunsaturated fatty acids with a double bond at the third carbon atom from the end of the carbon chain. Omega-9 fatty acids (ω-9 fatty acids or n-9 fatty acids) are a family of unsaturated fatty acids which have a final carbon-carbon double bond in the omega-9 position; that is, the ninth bond from the methyl end of the fatty acid.

The hemp oil used in the supplements described herein can contain whole hemp oil. The hemp oil used in the in the supplements described herein can, for example, contain omega-6 linoleic acid (omega-6 LA), omega-3 alpha-linoleic acid (omega-3 ALA), gamma-linolenic acid (omega-6 (GLA), stearidonic acid (omega-3 (SDA), omega-9 fatty acids, and combinations thereof. The hemp oil extract can contain at least three, at least four, at least five, at least six of the following: hemp oil, omega-6 linoleic acid (omega-6 LA), omega-3 alpha-linoleic acid (omega-3 ALA), gamma-linolenic acid (omega-6 (GLA), docosahexaenoic acid (DHA), stearidonic acid (omega-3 (SDA), or omega-9 fatty acids.

The amounts of hemp oil, omega-6 linoleic acid (omega-6 LA), omega-3 alpha-linoleic acid, gamma-linolenic acid (omega-6 (GLA), stearidonic acid (omega-3 (SDA), docosahexaenoic acid (DHA), or omega-9 fatty acids can vary. For example, a single serving of the supplements described herein can contain about 0.01 mg/Kg to about 25 mg/Kg, or about 0.05 mg/Kg to about 20 mg/Kg, or about 0.1 mg/Kg to about 15 mg/Kg, or about 0.1 mg/Kg to about 10 mg/Kg of the following: hemp oil, omega-6 linoleic acid (omega-6 LA), omega-3 alpha-linoleic acid (omega-3 ALA), gamma-linolenic acid (omega-6 (GLA), docosahexaenoic acid (DHA), stearidonic acid (omega-3 (SDA), or omega-9 fatty acids.

*Boswellia serrata*

*Boswellia serrata* is a plant that produces Indian frankincense. The plant is native to much of India and the Punjab region that extends into Pakistan.

The whole *Boswellia serrata* plants, or parts of the plants, such as the resin or gum tapped from the incision made on the trunk of the tree, can be used as a component of the supplements described herein. The resin of *Boswellia serrata* plants contains boswellic acids such as 1-keto-beta-boswellic acid (KBA), acetyl-1-keto-beta-boswellic acid (AKBA), beta-Boswellic acid (BA) and acetyl-beta-boswellic acid (ABA).

One method of preparing useful components (e.g., boswellic acids) from these plants involves extraction of *Boswellia serrata* resin with (1) hot isopropyl alcohol, followed by extraction with (2) a hot $C_1$-$C_6$ alcohol, e.g. isopropyl alcohol, or butanol, and concentration of the alcohol extract by (3) stripping off the alcohol solvent, to reduce the volume to about 50% of the original volume. The concentrate can then be (4) treated with an alkaline substance, e.g. alkali such as KOH or NaOH, with a pH of 9.5 or less, at a temperature ranging from room temperature to 60° C. (e.g., KOH at pH 9.5 and at 60° C.). Next, the process can involve (5) removing isopropyl alcohol, and washing the residue with an organic solvent, for example, with ether, ethyl acetate, or an ester or ketone solvent. The aqueous layer can then be (6) treated with hydrochloric acid to lower the pH to about pH 4. The precipitate (7) can then be obtained, and (8) washed with water. The washed precipitate can then be (9) dried at a temperature that is less than 50° C. One example of the organic solvent used in step 5 of this process is ethyl acetate.

The following is a more detailed example of a manufacturing process for obtaining boswellic acid.

1. Charge an extractor with 555 kg *Boswellia serrata* gum.
2. Charge isopropyl alcohol into the extractor to a level sufficient to cover the gum.
3. Pass steam into the jacket and maintain the temperature at 68-70° C. in the core body of the reactor.
4. Drain off the extraction fluid and concentrate it at 70° C. to strip off the isopropyl alcohol completely.
5. Charge isopropyl alcohol into the extractor to a level sufficient to cover the residue (e.g., 550 liters) and repeat the steps 3 and 4.
6. Repeat step 5
7. Charge 560 liters of 5 weight % aqueous KOH into the reactor, then stir at room temperature for 3 hours.
8. Wash with ethyl acetate 830 L.
9. Drain the ethyl acetate layer and collect aqueous layer.
10. Repeat step 8 and 9 two times with 550 L ethyl acetate and collect the aqueous layer each time.
11. Charge the aqueous layer (from steps 9 and 10) into a reactor.
12. Add slowly 6 N HCl to reduce the pH to about pH 3-4 (about 30 liters 6N HCl) while stirring at room temperature.
13. Allow a precipitate to form.
14. Add 1000 liters of water and let it stand at room temperature for up to 8 hours (or less depending on observation of precipitate formation).
15. Collect the precipitate (e.g., by draining into a nutsch filter and/or scooping out the precipitate), wash the precipitate with water.
16. Check for Boswellic acids in aqueous wash and if absent discard the wash.
17. Dry the precipitate at a temperature that is not above 50° C.

The Boswellic acids can be detected and quantified by HPLC using 1000 ml of Acetonitrile with 0.05 ml of glacial acetic acid as Mobile phase A, and 1000 ml water and acetonitrile (ratio 150:850) with 0.05 ml of glacial acetic acid as Mobile phase B. These Mobile phases should be mixed, filtered and degassed prior to use. The gradient program can be as follows:

| Time | A concentration | B concentration |
| --- | --- | --- |
| 0 min | 90% | 10% |
| 20 min. | 0% | 100% |
| 25 min. | 50% | 50% |
| 30 min. | 100% | 0% |

The final step can proceed for 30 min and then terminated.

The samples and standards (controls) for the HPLC assay can be prepared as follows:

Test Sample Preparation:

Weigh accurately about 200 mg of the sample and transfer into a 50 ml volumetric flask. Add 25 ml of methanol to dissolve the sample, and sonicate for 3 minutes, dilute to volume and mix.

Standard Preparation:

1. Beta-boswellic acid: weigh accurately about 25 mg of the standard and transfer into a 10 ml volumetric flask. Add 5 ml of methanol to dissolve the sample, and sonicate for 3 minutes. Dilute to volume and mix.

2. Acetyl-beta-boswellic acid: weigh accurately about 500 mg of standard and transfer into a 10 ml volumetric flask. Add 5 ml of methanol to dissolve the sample, sonicate for 3 minutes, dilute to volume, and mix.

3. 11-Keto-beta-boswellic acid: weigh accurately about 25 mg of the standard and transfer into a 25 ml volumetric flask. Add 15 ml of methanol to dissolve the sample, sonicate for 3 minutes, dilute to volume, and mix.

4. Acetyl-11-keto-beta-boswellic acid: weigh accurately about 25 mg of the standard and transfer into a 25 ml volumetric flask. Add 1 ml of methanol to dissolve the sample, sonicate for 3 minutes, dilute to volume, and mix.

Alternatively, weigh accurately about 25 mg of the standard (which contains known concentration of beta-boswellic acid) into 25 ml volumetric flask. Add 15 ml of methanol to dissolve the sample, sonicate for 3 minutes, dilute to volume, and mix.

Another procedure for isolating components (e.g, boswellic acids) from *Boswellia serrata* is provided as follows. The resin *Boswellia serrata* can be frozen at −30° C. overnight, then finely ground in a laboratory mill and extracted in a Soxhlet extractor with distilled dichloromethane for 16 h. For example, a 180 g amount of the finely ground resin can be extracted with about 1.5 liters of dichloromethane solvent. The solvent can be evaporated with the aid of a rotary evaporator at 40° C. under vacuum (about 10 mbar). The residue (raw extract) can be dissolved in 200 mL of diethyl ether and then extracted with 200 mL of 5% (m/v) aqueous KOH in a separatory funnel. After separating the phases, the alkaline aqueous phase can be extracted three times with 50 mL of diethyl ether each. The combined ethereal phases can be washed with brine (20 mL) and dried with $MgSO_4$. After filtration to remove the drying agent, the diethyl ether can be evaporated under vacuum in a rotary evaporator. The remaining oily residue is a neutral fraction of the extract. The alkaline aqueous phase from above can be cooled in an ice bath and carefully acidified with ice cold, concentrated aqueous hydrochloric acid. The mixture can become turbid milky through separation of insoluble acidic compounds. These can each be extracted three times with 50 mL of distilled diethyl ether. The combined extracts can then be washed with brine (20 mL) and dried over $MgSO_4$. After filtration to remove the drying agent, the solvent can be evaporated under vacuum. The remaining yellow to orange foam is the acidic fraction of the resin and it contains all lipophilic acids of the particular resin. The amounts of the neutral fraction and the acidic fraction depend strongly on the particular resin.

The amount of *Boswellia serrata* extract in the in the CG Medlife Supplement and the Sports Drink/Preventative Supplement can vary. For example, the amounts of *Boswellia serrata* extract per single serving can range from about 5 mg/Kg to about 100 mg/Kg, or from about 10 mg/Kg to about 80 mg/Kg, or from about 20 mg/Kg to about 65 mg/Kg. In many cases, the amount of *Boswellia serrata* extract can be about 48 mg/Kg per serving.

*Curcuma*/Turmeric

Turmeric (*Curcuma longa*) is a rhizomatous herbaceous perennial plant of the ginger family, Zingiberaceae. It is native in southwest India, and needs temperatures between 20 and 30° C. (68 and 86° F.) and a considerable amount of annual rainfall to thrive. Plants can be gathered annually for their rhizomes, and propagated from some of those rhizomes in the following season. When not used fresh, the rhizomes (rootstalks) can be boiled for about 30-45 minutes and then dried in hot ovens, after which they can be ground into a deep-orange-yellow powder commonly used as a spice in Indian cuisine, Pakistani cuisine and curries.

The whole turmeric (*Curcuma longa*) plants, or parts of the plants, such as the rhizomes, can be used as a component of the supplements described herein. One method of preparing useful components from these plants involves grinding of dried turmeric (e.g., 500 g) and separation through a vibrating sieving machine. Four different particle sizes can be separated: the 60 mesh (about 250 µm and smaller) size, 44 mesh (about 350 µm and small) size, 30 mesh (about 595 µm and smaller) size and above 30 mesh (about 595 µm and larger) size. The powders can be accumulated and then sealed separately with labeling for further analysis and processing.

Turmeric can be extracted with solvents using ethanol and water. For example, about 2 grams of each particle size can separately be mixed with 30 ml of ethanol and 30 ml of water, and then filtered. The filtrate is retained and can be concentrated as desired. The absorbance can be measured at 425 nm using a spectrophotometer and the extinction coefficient $\varepsilon_{425\ nm}=54954\ cm^{-1}M^{-1}$ can be used to determine the amount (concentration) of the curcumin obtained by the extraction.

The amount of turmeric extract in the in the CG Medlife Supplement and the Sports Drink/Preventative Supplement can vary. For example, the amount of turmeric extract per single serving can range from about 0.1 mg/Kg to about 20 mg/Kg, or from about 0.5 mg/Kg to about 14 mg/Kg, or from about 1 mg/Kg to about 8 mg/Kg. In many cases, the amount of turmeric can be about 4.5 mg/Kg per serving.

Black Cumin Seeds (*Nigella sativa*)

Black cumin seeds can be included in the supplements. The black cumin seeds can be from the species of *Nigella sativa*.

One method of preparing useful components from these plants involves grinding of dried black seed (e.g., 500 g) and separation through a vibrating sieving machine. Four different particle sizes can be separated: the 60 mesh (about 250 µm and smaller) size, 44 mesh (about 350 µm and small) size, 30 mesh (about 595 µm and smaller) size and above 30 mesh (about 595 µm and larger) size. The powders can be accumulated and then sealed separately with labeling for further analysis and processing. In some cases the powdered black cumin seeds can be boiled in water, for example, in an amount of 30 grams black cumin seeds per liter, for about 10-30 mins.

For example, the amount per single serving of black cumin seed extract in the CG Medlife Supplement and/or the Sports Drink/Preventative Supplement can range from about 0.1 mg/Kg to about 80 mg/Kg, or from about 0.5 mg/Kg to about 44 mg/Kg. or from about 1 mg/Kg to about 80 mg/Kg. In some cases, the amount of black seed can be about 60 mg/Kg per serving.

Pumpkin Seed Powder

Pumpkin seed powder in an amount of about 2.0 and 4.0 mg/100 g of body weight can be employed in the CG Medlife Supplement and/or the Sports Drink/Preventative Supplement. For example, the amount of pumpkin seed powder or pumpkin seed extract per single serving can range from about 0.1 mg/Kg to about 5.0 mg/Kg, or from about 0.5 mg/Kg to about 8.0 mg/Kg, or from about 1 mg/Kg to about 6 mg/Kg. In many cases, the amount of pumpkin seed powder or extract can be about 3.0 mg/Kg per serving.

One method of preparing useful components from these pumpkin seeds can involve grinding of dried pumpkin seed (e.g., 500 g) and separation through a vibrating sieving machine. Four different particle sizes can be separated: the 60 mesh (about 250 μm and smaller) size, 44 mesh (about 350 μm and small) size, 30 mesh (about 595 μm and smaller) size and above 30 mesh (about 595 μm and larger) size. The powders can be accumulated and then sealed separately with labeling for further analysis and processing. In some cases the pumpkin seed powder (e.g., 30 grams) can be boiled in one liter of water for 10-30 minutes, and such an extract can be used in the supplements.

Pepper

Black pepper, white pepper, green pepper, peppercorn, Madagascar pepper (English); pippali (Sanskrit); kali mirch (Hindi, Urdu); milagu (Tamil) can be used in the supplements. Black pepper fruits are the source of one of the world's most widely and frequently used spices. Black, white and green peppercorns all come from *Piper nigrum* and are popularly used as a hot and pungent spice for flavoring food. Black pepper is also used in traditional medicine, particularly for digestive ailments.

One method of preparing useful components from such peppers involves grinding of dried *Piper nigrum* L. (e.g., 500 g) and separation through a vibrating sieving machine. Four different particle sizes can be separated: the 60 mesh (about 250 μm and smaller) size, 44 mesh (about 350 μm and small) size, 30 mesh (about 595 μm and smaller) size and above 30 mesh (about 595 μm and larger) size. The powders can be accumulated and then sealed separately with labeling for further analysis and processing. For example, about 30 grams of pepper can be boiled in one liter of water for 10-30 minutes to prepare a pepper extract. In some cases up to about 5 mL/kg of such an extract can be used in the CG Medlife Supplement and/or the Sports Drink/Preventative Supplement.

*Artemisia ludoviciana* and/or *Artemisia princeps*

*Artemisia ludoviciana* is North American plant species in the daisy family. It is known by several common names, including silver wormwood, western mugwort, Louisiana wormwood, white sagebrush, and gray sagewort.

*Artemisia princeps*, or Japanese mugwort, is an Asian plant species in the sunflower family, native to China, Japan, and Korea.

The whole *Artemisia ludoviciana* and/or *Artemisia princeps* plants, or parts of the plants, such as the leaves, can be used as a component of the supplements described herein. One method of preparing useful components from these plants involves washing about 1 Kg dried leaves with water, and allowing the leaves to stand in water (20 liters) at room temperature for 3 days to effect extractions. Centrifugation (6000 r.p.m.) for 20 minutes can be used to remove residue. The residue can be washed twice with water (each 5 liters) and the washing liquid can be combined with the extracted supernatant. In one experiment the solid content in the combined solutions was 138.735 g (dry basis).

The combined solutions can be fractionated by ultrafiltration where the filter retains substances and compounds having a molecular weight of more than 200,000, for example, using a pressure of 3 kg/cm$^3$. The resulting residue can then be freeze-dried to obtain a brown powder (19.676 g). A similar treatment to that described above can be effected by using a membrane (XM 100 A) for retaining substances having a molecular weight of more than 100,000 to give a brown powder (20.835 g in one experiment).

In a second purification step, the first crude powder (e.g., 1.5 g) can be dissolved in water (5 ml) and transferred to a column (4.5×70 cm) packed with the gel filtration agent Sephadex G-200. Water (e.g., 600 ml) can be used for elution and the effluent can be divided into fractions (e.g., 3 ml each). In one experiment, fraction Nos. 27 to 60 were collected and combined and the combined fractions were freeze-dried to obtain a whitish powder (220 mg).

In a third purification step, this whitish powder (100 mg) can be dissolved in a 0.1 M Tris-HCl, pH 7.0 buffer solution (e.g., 5 ml; I=0.01) and transferred to a column (2.5×70 cm) packed with the ion exchange material DEAE-Sephadex A-50. Elution can be with a 0.1 M Tris-HCl buffer solution (300 ml; pH 9.0; containing 0.5 M NaCl) and the effluent can again be divided into fractions (e.g., 3 ml each). In one experiment, fraction Nos. 15 to 30 were collected and combined. The combined fractions can be freeze-dried to obtain a whitish amorphous powder (62.7 mg in one experiment) containing smaller amounts of impurities and having substantially the same interferon inducing activity when compared with the first whitish powder.

The amount of *Artemisia ludoviciana* and/or *Artemisia princeps* extract in the in the CG Medlife Supplement and the Sports Drink/Preventative Supplement can vary. For example, the amount of *Artemisia ludoviciana* and/or *Artemisia princeps* extract can range from about 0.1 mg/Kg to about 20 mg/Kg, or from about 0.5 mg/Kg to about 15 mg/Kg, or from about 1 mg/Kg to about 10 mg/Kg. In many cases, the amount of *Artemisia ludoviciana* and/or *Artemisia princeps* extract can be about 5 mg/Kg per serving.

Astragalus

*Astragalus propinquus* (syn. *Astragalus membranaceus*, also known as huáng qí, běi qí, or huáng huā huáng qí) is a perennial, flowering plant in the family Fabaceae. It is one of about 50 fundamental herbs used in traditional Chinese medicine.

The whole plant or parts of the plant, such as the roots, can be used as a component of the supplements described herein. One method of preparing useful components of *Astragalus membranaceus* involves extraction of the roots with 95% ethanol. For example, 10 kg of the roots of *Astragalus membranaceus* can be extracted with 100 liters of 95% ethanol under reflux for 4 hours. The alcoholic solution can be discarded and the vegetal material can be extracted with 100 liters of 20% aqueous ethanol. The hydroalcoholic extract solution can be concentrated under vacuum to a 10 liters volume at a temperature of 50° C. The aqueous solution can be decolorized at 50° C. with 100 g of activated vegetal charcoal. The solution can then be diluted under continuous agitation with 40 liters of 95% ethanol. The resulting precipitate can be collected by decanting off the supernatant. The supernatant is discarded and the precipitate is set aside.

The solid vegetal material obtained by extraction with 20% ethanol, as described above, can be treated with 50 liters 1N NaOH and left to stand at 14° C. for 12 hours. The solution and the vegetal material can then be neutralized at pH 7 and heated to the boiling point for 2 hours. The vegetal material can be filtered at a temperature of about 70° C. and the extracted liquid can be decolorized with 100 g of activated vegetal charcoal. The extracted liquid can then be concentrated to about 8 liters. After filtering to remove the flocculated material, the concentrate can be decanted into 10 liters of 95%0/ethanol. The resulting solid precipitate can be collected and added to the material obtained above from the neutral hydroalcoholic extraction.

The pooled solid materials can be dissolved in 5 liters of water and the resulting solution can be poured under vigorous shaking into 20 liters of isopropanol. After drying under vacuum overnight, 420 g of the final product can be obtained, which consists of a polysaccharide mixture containing substances with molecular weights ranging from 12,000 to 500,000 daltons.

The amount of *Astragalus membranaceus* extract in the in the CG Medlife Supplement and the Sports Drink/Preventative Supplement can vary. For example, the amount of turmeric extract can range from about 1 mg/Kg to about 30 mg/Kg, or from about 3 mg/Kg to about 25 mg/Kg, or from about 5 mg/Kg to about 20 mg/Kg. In many cases, the amount of *Asiragalus membranaceus* extract can be about 14 mg/Kg per serving.

Fenugreek

Fenugreek is an annual plant in the family Fabaceae, with leaves consisting of three small obovate to oblong leaflets. It is cultivated worldwide as a semiarid crop, and its seeds are a common ingredient in dishes from the Indian Subcontinent in South Asia. The whole plant or parts of the plant, such as the seeds, can be used as a component of the supplements described herein.

For example, the seeds can be powdered using pestle and mortar and 100 g of the powder can be extracted with hexane to remove lipophilic compounds using a Soxhlet apparatus. To remove pigments and to deactivate enzymes, the defatted powder can be boiled in ethanol for 20 min. This treated powder can then be soaked in 10 liters of water and the pH can be adjusted to 3.5 using 0.5 M hydrochloric acid. The mixture can be stirred by a mechanical stirrer for 12 h and then filtered through filtration paper. The filtrate can be centrifuged (5000 g) and the supernatant concentrated in vacuum to 50% of its initial volume. The resulting supernatant solution can be mixed with the same volume of 96% ethanol and stored in a refrigerator for 4 h. The precipitated mucilage can then be sedimented by centrifugation (5000 g). The collected mucilage can be re-suspended in distilled water, agitated for 20 min and re-precipitated one more time to eliminate chloride ions and other impurities. Finally the residue can be washed with diethyl ether and acetone and dried overnight at 45° C., resulting in an off-white powder.

The amount of fenugreek extract in the in the CG Medlife Supplement and the Sports Drink/Preventative Supplement can vary. For example, the amount of fenugreek extract can range from about 0.1 mg/Kg to about 20 mg/Kg, or from about 0.5 mg/Kg to about 15 mg/Kg, or from about 1 mg/Kg to about 10 mg/Kg. In many cases, the amount of fenugreek extract can be about 5.5 mg/Kg per serving.

Guinea Hen Weed Root

Guinea hen weed, known in South Americans as anamu, is an herb that is indigenous in the Amazon rainforest and the tropical areas of the Caribbean, Central and South America and Africa. Its botanical name is *Petiveria alliacea*. In Jamaica, it has several names—guinea hen weed, guinea hen leaf, garlic weed or gully root. Plants can be gathered annually for their rhizomes, and propagated from some of those rhizomes in the following season. When not used fresh, the rhizomes (rootstalks) can be boiled for about 30-45 minutes and then dried in hot ovens.

The whole Guinea hen weed root, or parts of the plants, such as the rhizomes, can be used as a component of the supplements described herein. One method of preparing useful components from these plants involves grinding of dried guinea hen weed (e.g., 500 g) and separation through a vibrating sieving machine. Four different particle sizes can be separated: the 60 mesh (about 250 µm and smaller) size, 44 mesh (about 350 µm and small) size, 30 mesh (about 595 µm and smaller) size and above 30 mesh (about 595 µm and larger) size. The powders can be accumulated and then sealed separately with labeling for further analysis and processing.

Guinea hen weed root can be extracted with solvents using ethanol and water. For example, about 2 grams of each particle size can separately be mixed with 30 ml of ethanol and 30 ml of water, and then filtered. The filtrate can be retained and can be concentrated as desired. The absorbance can be measured at 425 nm using a spectrophotometer and the extinction coefficient $\varepsilon_{425\ nm}=54954\ cm^{-1}\ M^{-1}$ can be used to determine the amount (concentration) of the Guinea hen weed root obtained by the extraction.

The amount of Guinea hen weed root extract used in the in the CG Medlife Supplement and the Sports Drink/Preventative Supplement can vary. For example, the amount of Guinea hen weed root extract per single serving can range from about 0.1 mg/Kg to about 20 mg/Kg, or from about 0.5 mg/Kg to about 14 mg/Kg, or from about 1 mg/Kg to about 8 mg/Kg. In many cases, the amount of turmeric can be about 4.5 mg/Kg per serving.

Mushrooms

The supplements described herein can include mushrooms, either whole mushrooms or parts of mushrooms, such as the caps. For example, whole mushrooms (or parts thereof), can be processed for inclusion in the supplements described herein. The mushrooms in the mushroom extract can include Red Reishi, Shitake, Maitake, *Ponderosa armillaria, Gigantea calvatia, Veriscolor coriolus, Applanatum ganoderma, Velutipes flammulina*, or any combination thereof. For example, the supplements can contain at least two of these mushroom extracts, or at least three of these mushroom extracts, or at least four of these mushroom extracts, or at least five of these mushroom extracts, or at least six of these mushroom extracts, or seven of these mushroom extracts. In some cases, the supplements contain all of these mushroom extracts.

The amounts of Red Reishi, Shitake, Maitake, *Ponderosa armillaria, Gigantea calvatia, Veriscolor coriolus, Applanatum ganodernma*, or *Velutipes flammulina* extract within the CG Medlife Supplement and/or Sports Drink/Preventative Supplement can vary. For example, the amounts of each of these extracts can range from about 0.01 mg/Kg to about 20 mg/Kg, or from about 0.05 mg/Kg to about 10 mg/Kg. or from about 0.1 mg/Kg to about 8 mg/Kg.

Red Reishi

The lingzhi mushroom or reishi encompasses several fungal species in the genus *Ganoderma*, most commonly the closely related species *Ganoderma lucidum, Ganoderma tsugae*, and *Ganoderma sichuanense*. In East Asia, *Ganoderma sichuanense* enjoys special veneration, where it has been used as a medicinal mushroom in traditional Chinese medicine for more than 2,000 years, making it one of the oldest mushrooms known to have been used medicinally. Though there are up to six different types of reishi, all classified by color, herbalists generally call red reishi the most potent and medicinal variety.

One method of preparing useful components of red reishi is to dry whole mushrooms (or parts thereof) and then grind them to form a dry particulate. Alpha-tocopherol acetate and a surfactant, alpha-tocopherol acid succinate-PEG 1000 (TPGS™, Eastman), can be mixed together with the mushroom particles and stirred in dry ethanol at 35° C. until a homogenous suspension was obtained. The suspension can be mixed with sorbents to remove undesired components (e.g., water). The paste that forms can be carefully mixed, then transferred to a granulator, and mixed with Methocel K4M, Methocel E15 and polyvinylpyrrolidone (PVP). The formed blend can then be granulated with ethyl alcohol until a proper granulate was obtained. The granular preparation can be dried at temperature that is no more than 35° C. (to prevent evaporation of volatile aromatic compounds of extract) until the solvent was totally evaporated.

The dried granulate can be sieved, mixed with microcrystalline cellulose, and formed into Tablets. Tablets can have a hardness of between 10 kg and 12 kg and a friability of less than 1%. Tablet dissolution can be determined in accordance with USP 23 (37° C., 100 rpm, 900 ml water). Tablets will typically dissolve in about 6 hours in apparatus 2 (more than 80% dissolved).

The amount of red reishi extract in the in the CG Medlife Supplement and the Sports Drink/Preventative Supplement can vary. For example, the amount of red reishi extract can range from about 0.1 mg/Kg to about 20 mg/Kg, or from about 0.5 mg/Kg to about 15 mg/Kg, or from about 1 mg/Kg to about 10 mg/Kg. In many cases, the amount of red reishi extract can be about 4 mg/Kg per serving.

Shitake

The shitake (*Lentinula edodes*) is an edible mushroom native to East Asia.

One method of preparing useful components of shittake mushrooms is to dry whole mushrooms (or parts thereof) and then wash the mushrooms (e.g. 300 g) with boiling industrial methylated spirits (IMS, e.g., 2 liters). The mixture is filtered to recover the IMS. The resulting precipitate can be washed with water and then filtered, with the water phase being discarded. The resulting precipitate was then washed with approximately 3 to 5 liters of hot water (temperature about 80° C. to less than 100° C.). This wash step was repeated three times. Following washing, the water can be removed by means of a rotary evaporator to give a crude lentinan gel. The gel can be dissolved in a mixture of 1-butyl-3-methylimidazolium chloride (e.g., 50 g) and water (e.g., 50 ml), with any remaining solids being filtered off. The 1-butyl-3-methylmtdazolium chloride solution can then be carefully added to the recovered IMS to precipitate out the lentinan, which was then dried and ground to a powder. A yield of about 1.5 g can be obtained. Water soluble lentinan polysaccharides contained derived from Chinese freeze dried mushroom extracts can be isolated with over 90% purity as measured on a gel-HPLC column.

The amount of shitake extract in the in the CG Medlife Supplement and the Sports Drink/Preventative Supplement can vary. For example, the amount of shitake extract can range from about 0.1 mg/Kg to about 15 mg/Kg, or from about 0.5 mg/Kg to about 10 mg/Kg, or from about 1 mg/Kg to about 10 mg/Kg. In many cases, the amount of shitake extract can be about 2 mg/Kg per serving.

Maitake

*Grifola frondosa* (maitake) is a polypore mushroom that grows in clusters at the base of trees, particularly oaks. The mushroom is commonly known among English speakers as hen-of-the-woods, ram's head and sheep's head. Maitake is typically found in late summer to early fall.

One method of preparing useful components of maitake mushrooms is to thoroughly dry whole mushrooms (or the fruiting bodies, sporophores, thereof), for example, in a desiccator and grind the dried mushrooms into a powder. Ethanol (35%) can be added to the powder, and used as an extraction solvent. Several extractions with 35% ethanol can be performed the extract is almost colorless. The extracted solution can be concentrated (e.g., to about 35 to 40 ml) and allowed to rest overnight in the refrigerator. A white precipitate typically forms (mainly mannitol and sterol), which can be removed, for example, by filtration. Water (e.g., 100 ml) can be added to the filtrate, whereupon a red-brown oily layer and a turbid aqueous layer forms. The aqueous layer was discarded and the oily layer is washed several times with water to remove the water-soluble substances, as well as the ethanol. The oily layer was dissolved methanol (e.g., 100 ml) and cooled. Colorless crystals can form and can be removed. The methanol can be evaporated, and the residue (e.g., about 6 gm, of an oil) can be shaken with 1 percent KOH and ether. The alkali layer is discarded and the washing with 1% KOH can be repeated until the alkali solution remained almost colorless. The ether layer can be washed with water. The ether layer can then be dried over $CaCl_2$. A red-brown syrup can be obtained by evaporating the solvent, to yield crystals when cooled. For further purification, the dried ether solution can be directly chromatographed on alumina. Colored impurities are absorbed as the top band and grifolin can be obtained from the ether eluate. In one experiment the yield was 2 gm.

A slightly modified method, with lead acetate used before the addition of methanol, has been employed in the preparation of larger amounts. In addition to mannitol and sterol, a hemin-like substance, and crystals possessing hydrocarbons (m.p. 1450 or 62-63° C.) and occidenol diptrocarpaceae (m.p. 151-152° F. or 66-67° C.) have been obtained as by-products during various extraction procedures.

Crude grifolin from the eluate can be further purified by drying under reduced pressure and dissolution in a small amount of petroleum ether. The solution can be cooled overnight, then rapidly filtered through a previously cooled glass filter. The product can be washed several times with ice-cold petroleum ether. Fine colorless needles, exhibiting a feature characteristic of Liesegang rings, can be obtained (m.p. 40° F. or 4° C.). Distillation under reduced pressure (e.g., 150° F./65° C. and 1 mm Hg) was exceedingly slow and unsuitable as a means.

The amount of maitake extract in the in the CG Medlife Supplement and the Sports Drink/Preventative Supplement can vary. For example, the amount of maitake extract can range from about 0.1 mg/Kg to about 15 mg/Kg, or from about 0.5 mg/Kg to about 10 mg/Kg, or from about 1 mg/Kg to about 10 mg/Kg. In many cases, the amount of maitake extract can be about 2 mg/Kg per serving.

Prickly Pear Fruit

Prickly pear fruit or extracts thereof can be used in the supplements described herein.

Prickly pear fruit belongs to the genus *Opuntia* spp., and is the most abundant of the Cactaceae family. Prickly pear is grown throughout the Americas as well as the central area of the Mediterranean, Europe, Asia, Africa, and Australia. The *Opuntia* species display flattened stems called "pencas" or cladodes. The cactus pear fruit also called prickly pear fruit is an oval elongated berrn, with a thick pericarp, a juicy pulp with a considerable number of seeds and a semi-hard rind with thorns. The pericarp and the edible pulp may have different colors such as green, greenish white, canary yellow, lemon yellow, red, cherry-red, or purple hues. The average weight of prickly pears fruits varies from 100 to 160 g depending on the origin site and cultivation.

The usable part of the fruit is composed of peel (48%-52%) and pulp (48%-52%). The pulp can be further subdivided into seeds and strained pulp (44%-45%), the latter being the basis for fruit and juice products. To extract the juice, place the 12 "husked" prickly pears into a blender or food processor and pulse until liquefied. Place the juice into a fine mesh sieve and push out the juice into a pitcher or bowl with distilled water.

The amount used in the supplements can vary. For example, an individual dose of prickly pear juice can be about 5 mg/kg to about 5 ml per kg.

Multi-Minerals

Note that the "Multi-Minerals" that are part of the employed amino acids listed in Table 1 include approximate equal parts by weight of the following: Antimony, Barium, Beryllium, Bismuth, Boron, Bromine, Cadmium, Calcium Carbon, Cerium, Cesium, Chloride, Chromium, Cobalt, Copper. Dysprosium, Erbium, Europium, Fluorine, Gadolinium, Gallium, Germanium, Gold, Hafnium, Holmium, Indium, Iodine, Iridium, Iron, Lanthanum, Lithium, Lutetium, Magnesium, Manganese, Molybdenum, Neodymium, Nickel, Niobium, Osmium. Palladium. Phosphorous, Platinum. Potassium, Praseodymium, Rhenium, Rhodium, Rubidium, Ruthenium, Samarium, Scandium, Selenium, Silicon, Silver, Sodium, Strontium, Sulfur, Tantalum, Tellurium, Terbium, Thulium, Thorium, Tin, Titanium, Tungsten, Vanadium, Ytterbium, Yttrium, Zinc elemental, Zirconium.

Flavoring Agents

The supplement can also contain any one of a variety of known flavoring agents. For example, the supplement can contain flavoring agents. Exemplary flavoring agents include strawberry flavoring, plum extract, complex sugars such as fructose, and other flavoring agents known in the arts, such as polysaccharide.

Artificial sweeteners can also be used. It may be desirable, however, for the supplement to be comprised substantially, even entirely, of naturally occurring sweeteners and/or no sweeteners. There is no real limit on the amount of flavoring agent but the supplements have a mild taste that generally needs no added flavoring agents. Enough flavoring agent can be included to produce a supplement having a particular, desirable taste. Methods are available that can be used to determine what flavoring agents, and levels thereof, should be included in the supplement. The composition can be provided free of flavoring agents as well.

Methods of Making the Supplements

The CG Medlife supplement and the Sports Drink/Preventative supplement can be made by a variety of procedures. In general, these supplements do not contain added water or other liquids, however, the final supplement can be diluted as desired into liquids as desired. Instead of dissolving all the ingredients in a suitable solvent, the liquids that make up the CG Medlife supplement and the Sports Drink/Preventative supplement are from the components that form the basis of these supplements. These components are preferably fresh components, although in some cases the components can be dried as indicated above.

In general, each class of nutrient is separately combined with all members of the class. For example, the amino acids of the amino acid blend are typically combined together prior to mixing with the other classes of components. Similarly, the components of the coconut extract are mixed or prepared before addition and combination with the other classes of components. The alcohol blend, the cannabinoid blend, the hemp plant extract, a *Boswellia serrata* extract, a curcuma/turmeric blend, an *Artemisia ludoviciana* extract, the *Astragalus* extract, the fenugreek extract, and/or the mushroom extract blend, are also separately made before mixing these classes of nutrients together.

The oil-containing and/or waxy components such as the glycerin, the coconut extract, alcohol blend, the hemp plant extract, or a combination thereof can be used to solubilize and homogenize the solids such as the amino acid blend, the cannabinoid blend, the *Boswellia serrata* extract, the curcuma/turmeric blend, the *Artemisia ludoviciana* extract, the *Astragalus* extract, the fenugreek extract, the mushroom extract blend, or a combination thereof. When oil-containing/waxy components are combined with solids, the combination can be mildly heated (e.g., up to 45-60° C.) to help release useful nutrients from the plant cells and plant material of the mixture. The combination of components in the supplements can be mixed thoroughly to homogenize the mixture and facilitate release of nutrients for easy absorption by the recipient. Mixtures of components can be pressed, or centrifuged to collect solubilized nutrients and sediment undesirable debris. Sediments from such centrifugation can be washed with some of the oil-containing components to insure that the majority of nutrients are extracted.

The amounts, ratios, portions, and mg/Kg recited herein for the various ingredients can be varied from those expressly recited herein. The wisdom and experience of a prescribing medical person can appropriately manage the portions, concentrations and administrative doses of the ingredients and compositions herein.

The CG Medlife supplement and the Sports Drink/Preventative supplement so produced is generally a liquid that can be taken in various amounts. For example, a single serving can range from at least about one-half fluid oz., or at least about 1 fluid oz., or at least 2 fluid oz., or at least 4 fluid oz. In some instances, up to about 8 oz. can be taken in a single serving. Although the CG Medlife supplement and the Sports Drink/Preventative supplement are typically taken once per day, in some instances, a recipient can take a single serving twice a day or three times a day. In other instances, a recipient can take either of these supplements every other day, three times a week, twice a week, or once a week.

Additional Ingredients

The supplements described herein can also contain additional ingredients. For example, the supplements can include extracts from plants such as yew, pine, hemlock, ginger, poppy, or combinations thereof. The supplements can also contain ingredients such as vinca alkaloids (e.g., benzophenanthridine alkaloids), phenolics, xanthones, other terpenoids, paclitaxel, carnosic acid, Noscapine, phytoalexins, sulforaphane, lutcolin, betulinic acid, lunasin, plumbagin, gallic acid-based steroidal phenstatin analogs, cryptotanshinone, ursolic acid, coumarins, ginsenosides, withanolides, paclitaxel, carboplatin, pomolic acid, 1,4-naphthoquinones (e.g., from Diospyros L.), 4-shogaol (e.g., from ginger), sanguinarine, α-mangostin, magnolol, or any combination thereof (see, e.g., Park, EXCLI Journal 11:386-389 (2012) for further information on some of these ingredients).

Carrier

The supplements described herein are generally liquid formulations that require no additives, additional solvents, or carriers. However, the supplements can also be dry or concentrated formulations that can be diluted, combined or dissolved in a carrier. For example, the components and/or the completed supplement formulations can be freeze dried or concentrated to reduce the volume of the supplements (e.g., for ease of shipping or to generate a desired serving size). Such dry or concentrated supplement formulations can be combined with a carrier.

The carrier can be any substance that can form a homogenous mixture with the supplement components, and that can be dispensed in a manner to provide a predetermined serving size. The carrier should not interfere with any of the beneficial ingredients of the supplement so as to inhibit the desired activity. The amount of carrier is entirely within the discretion of the formulator, although higher levels of carrier may excessively dilute the supplement. In addition, certain levels of carrier may be used in order to obtain a desired serving size, a desired taste, or a desired texture or consistency. For example, the supplement can comprise about 10 wt % carrier to about 50 wt %.

The supplement can include a number of additional ingredients, such as preservatives, coloring agents, thickening agents, and other agents typically used in such supplements and known to those of skill in the art, that do not affect the activity of the above described active ingredients.

The supplement can be prepared for oral administration, and can be in the form of a liquid drink. The supplement can be formulated to be taken as a daily supplement. For instance, the serving size can be at least about one-half fluid oz., or at least about 1 fluid oz., or at least 2 fluid oz., or at least 4 fluid oz. For example, when the supplement is provided with a 1 fl. oz. serving size, a full month supply can be sold in a single 32 fl. oz. bottle. These volumes correspond to the supplement in a drinkable fluid. It is contemplated that the consumer may shake the supplement prior to consumption in order to obtain a more homogenous mixture. It also is contemplated that the supplement could be diluted by the consumer. Of course, the supplement could also be diluted by the manufacturer. For instance, the supplement could be diluted and sold as a beverage, or it could be added to a beverage prior to sale.

The supplement could also be provided as a gel, capsule, or tablet in which case the serving size could be reduced to below one ounce, or even below one-half ounce.

When formulated for human consumption, the supplement should be free from any substances that are unsuitable for human consumption. Substances that are typically present only in topically applied compositions that render the composition unsuitable for consumption can be eliminated from the supplement. For example, some substances that can be excluded from the composition include emollients, petroleum-based substances, and fragrances and perfumes that are unintended and unsuitable for human consumption.

Methods of Administration

Also described herein is a method of administering any of the supplements described herein to a subject. The subject can be a human, domesticated animal, experimental animal, or zoo animal.

The supplements can be liquid or solid. For example, the compositions can be dried and mixed with foods. Typically the supplements are in liquid form.

The supplements can be administered in an amount effective to reduce pain, reduce the symptoms of disease, increase energy, improve sleep patterns, increase activity levels, reduce extremity numbness, improve digestion, reduce the incidence or severity of headaches, reduce the frequency or severity of seizures, or combinations thereof, compared to healthy subjects, compared to a subject of the same species that does not receive the supplement, or compared to the subject's own experience prior to taking the supplements.

For example, a single serving of the supplement can be about 0.25 fluid ounces to about 12 fluid ounces, or about 0.5 fluid ounces to about 8 fluid ounces, or 1 fluid ounces to about 6 fluid ounces.

The supplements can be administered or taken at least once per week for four weeks. In some the supplements are routinely administered or ingested daily, biweekly, triweekly, weekly and/or via a sustained regimen over time (e.g., over one or more months, or over one or more years).

The following Examples provide exemplary formulations of health supplements. These formulations are merely exemplary, and should not be construed as limiting the invention which is defined by the claims only.

Example 1: Generic Health Supplement Formulation

This Example describes a generic form of the health supplement formulation, which is referred to as the CG Generic Supplement. The formulation has the following composition where the components are numbered 1-14.

1) Pharmaceutical grade vegetable glycerin oil.
2) Synthetic MCT (medium chain triglyceride) oil
3) Fulvic acid containing minerals and amino acids (e.g., about 75 minerals and about 11 amino acids
4) 100% Raw coconut oil
5) Strawberry flavoring
6) *Cannabis* bud containing THC (tetrahydrocannabinol)/hash
7) *Cannabis* leaf containing CBD (cannabidiol)
8) *Cannabis* matter for acids
9) *Cannabis* seeds
10) Turmeric root/plant and/or black cumin seeds (*Nigella sativa*)
11) Sweet wormwood (*Artemisia annua*) whole plant
12) *Boswellia serrata* whole plant
13) Glycine
14) 100% Hemp Seed Oil The following procedure is used to prepare the supplement.

Component #1 (128 ounces), component #14 (64 ounces), and component #2 (32 ounces) are mixed together. Then component #4 (32 oz) is added and the preparation is mixed well. This mixture is referred to as Part 1. Part 1 is then divided in two to generate a first half (96 ounces) and a second half (96 ounces).

A first half of Part 1 (96 oz) is mixed with component #6 (16 oz) and #9 (1 oz) with heat up to about 118° F. (47-48° C.) to combine the ingredients, and thereby form Part 2.

To form Part 3, the second half of Part 1 is mixed with component #7 (16 ounces) and with #9 (1 ounce) with heat up to about 118° F. (47-48° C.) to combine the ingredients.

Part 4 is prepared by mixing component #3 (64 oz) and component #8 (16 oz) and centrifugation using a cold centrifuge (about 4° C.) to remove debris (300-1200 rpm).

Part 5 is formed by mixing together component #4 (110 oz), component #5 (1 oz), and then mixing this well with component #6, component #7 (1 oz). After mixing well, component #9 (¼ oz) is added with mixing. Then component #13 (2 cups) is added with mixing, followed by component #10 (5 cups each of turmeric root/plant and black cumin seed). After mixing well, component #11 (7 cups) is added with mixing followed by component #12 (5 cups). The Part 5 mixture is mixed well with heat up to about 118° F. (47-48° C.) to combine the ingredients.

Part 6 is formed by mixing part 2 with part 3 using a cold centrifuge (about 4° C.) to remove debris (300-1200 rpm).

Part 7 is formed by mixing part 6 with part 4 using a cold centrifuge (about 4° C.) to remove debris (300-1200 rpm).

Part 8 is formed by mix part 7 with part 5 using a cold centrifuge (about 4° C.) to remove debris (300-1200 rpm).

All of the Parts are now mixed together to form about 2 gallons of the healthful supplement (CG Generic Supplement).

Example 2: Healthful Supplement Formulation

This example describes a more detailed version of a CG Medlife Supplement that contains optimal blends and ratios of specific ingredients.

The CG Medlife Supplement contains a series of nutrient types including an amino acid blend, a coconut extraction, a vegetable glycerin extract, an alcohol blend, a cannabinoid blend, a hemp plant extract, a *Boswellia serrata* extract, a curcuma/turmeric blend, an *Artemisia ludoviciana* extract, and a mushroom extract blend. The CG Medlife Supplement is 100% pure, with a slightly alkaline pH of 7.0 to 7.8. It has a mild taste.

The composition of the CG Medlife Supplement is provided in Table 1 and the components are discussed below the table.

TABLE 1

| CG Medlife Supplement | | | |
|---|---|---|---|
| Component | mg per Kg Body Weight (1 Serving) | mg per 70 Kg | mg per 100 Kg |
| Amino Acids | | | |
| Alanine | 5.8 | 406 | 588 |
| Arginine | 8.18 | 572.6 | 818 |
| Aspartic Acid | 1.092 | 76.44 | 1092 |
| Cystine | 2.88 | 201.6 | 288 |
| Glutamic Acid | 2.065 | 144.55 | 206.5 |
| Glycine | 3.78 | 264.6 | 378 |
| Histidine | 2.7 | 189 | 270 |
| Isoleucine | 7 | 490 | 700 |
| Lysine | 8 | 614 | 854 |
| Leucine | 10.91 | 763.7 | 1091 |
| Methionine | 2.76 | 193.2 | 276 |
| Phenylalanine | 11.2 | 784 | 1120 |
| Serine | 11.2 | 784 | 1120 |
| Proline | 7.32 | 512.4 | 732 |
| Threonine | 5.7 | 399 | 570 |
| Tryptophan | 1.87 | 130.9 | 187 |
| Tyrosine | 4.92 | 344.4 | 492 |
| Valine | 7.22 | 505.4 | 722 |
| Fulvic-humic acids | 20 | 1400 | 2000 |
| Multi-minerals | 20 | 25 | 30 |
| Coconut Extractions | | | |
| Caprylic Acid | 15 | 1050 | 1500 |
| MCT | 25 | 1750 | 2500 |
| Coconut Oil | 40 | 2800 | 4000 |
| Vegetable Glycerin | | | |
| glycerin | 45 | 3150 | 4500 |
| Alcohol Blend | | | |
| Alpha-Humulene | 2.5 | 175 | 250 |
| Alpha-Phellandrene | 10 | 700 | 1000 |
| Alpha-pinene | 4.5 | 315 | 450 |
| Alpha-Terpinene | 2.5 | 175 | 250 |
| Alpha-Terpinolene | 26 | 1820 | 2600 |
| Beta-Myrcene | 0.70 | 49 | 70 |
| Beta-pinene | 5 | 350 | 500 |
| Camphene | 0.6 | 42 | 60 |
| Cis-Ocimene | 2 | 140 | 200 |
| Delta-3 Carene | 1.1 | 77 | 110 |
| Limonene | 30 | 2100 | 3000 |
| Sabinene | 2.5 | 175 | 250 |
| Trans-Caryophyllene | 1.40 | 98 | 140 |
| Trans-Ocimene | 1.1 | 77 | 110 |
| Y-Terpinene | 1.5 | 105 | 150 |
| 1.8-Cineole | 1.8 | 126 | 180 |
| Perillyl alcohol | 1 | 70 | 100 |
| Cannabinoids | | | |
| THC | 10 | 700 | 1000 |
| THC-A | 15 | 1050 | 1500 |
| CBD | 6 | 420 | 600 |
| CBDA | 5 | 350 | 500 |
| CBG | 6 | 420 | 600 |

TABLE 1-continued

| CG Medlife Supplement | | | |
|---|---|---|---|
| Component | mg per Kg Body Weight (1 Serving) | mg per 70 Kg | mg per 100 Kg |
| CBC | 5 | 350 | 500 |
| CBN | 6 | 420 | 600 |
| Whole Plant | 1000 | 1500 | 2000 |
| Cold Pressed Plant Oil | | | |
| Oil from Whole Hemp Plant with Seeds Included | 5 | 350 | 500 |
| Omega-6 LA | 7 | 490 | 700 |
| Omega-3 ALA | 2.5 | 175 | 250 |
| Omega-9 | 2 | 140 | 200 |
| Omega-6 GLA | 0.5 | 35 | 500 |
| Omega-3 SDA | 0.25 | 175 | 250 |
| *Boswellia serrata* | | | |
| *Boswellia serrata* extract | 48 | 3360 | 4800 |
| *Curcuma*/Turmeric | | | |
| *Curcuma*/Turmeric extracts | 4.5 | 315 | 450 |
| *Artemisia ludoviciana* | | | |
| *Artemisia ludoviciana* extract | 5 | 350 | 500 |
| Mushroom Extracts | | | |
| *Ponderosa armillaria* | 1-2 | 70-140 | 100-200 |
| *Gigantea calvatia* | 1-2 | 70-140 | 100-200 |
| *Veriscolor coriolus* | 1-2 | 70-140 | 100-200 |
| *Applanatum ganoderma* | 1-2 | 70-140 | 100-200 |
| *Velutipes flammulina* | 1-2 | 70-140 | 100-200 |
| Shitake | 1-2 | 70-140 | 100-200 |
| Red Reishi | 2-4 | 140-280 | 200-400 |

In some cases Ajulemic acid is added, or used in place of a cannabinoid. For example, a single serving of the supplement can contain about 1 mg/Kg Ajulemic acid.

Example 3: Sports Drink Formulation

This example describes a Sports Drink Formulation is a preventative formulation that contains many of the ingredients of the CG Medlife Supplement described in Example 2, but that does not contain psychoactive amounts of cannabis to or cannabinoids.

The Sports Drink/Preventative formulation contains a series of nutrient types including an amino acid blend, a coconut extraction, a vegetable glycerin extract, an alcohol blend, a cannabinoid blend (without THC), a hemp plant extract, an *Astragalus* extract, a fenugreek extract, and a mushroom extract blend. The Sports Drink/Preventative is 100% pure, with a slightly alkaline pH of 7.0 to 7.8. It has a mild taste.

The composition of the Sports Drink/Preventative is provided in Table 2 and the components are discussed below the table.

TABLE 2

| Component | mg per Kg Body Weight (1 Serving) | mg per 70 Kg | mg per 100 Kg |
|---|---|---|---|
| Amino Acids | | | |
| Alanine | 5.8 | 406 | 588 |
| Arginine | 8.18 | 572.6 | 818 |
| Aspartic Acid | 1.092 | 76.44 | 1092 |
| Cystine | 2.88 | 201.6 | 288 |
| Glutamic Acid | 2.065 | 144.55 | 206.5 |
| Glycine | 3.78 | 264.6 | 378 |
| Histidine | 2.7 | 189 | 270 |
| Isoleucine | 7 | 490 | 700 |
| Lysine | 8 | 614 | 854 |
| Leucine | 10.91 | 763.7 | 1091 |
| Methionine | 2.76 | 193.2 | 276 |
| Phenylalanine | 11.2 | 784 | 1120 |
| Serine | 11.2 | 784 | 1120 |
| Proline | 12 | 732 | 1096 |
| Threonine | 15 | 1050 | 1500 |
| Tryptophan | 4 | 280 | 400 |
| Tyrosine | 6 | 492 | 792 |
| Valine | 26 | 505.4 | 2600 |
| Fulvic-humic acids | 20 | 1400 | 2000 |
| Multi-minerals | 20 | 25 | 30 |
| Coconut Extractions | | | |
| Caprylic Acid | 15 | 1050 | 1500 |
| MCT | 25 | 1750 | 2500 |
| Coconut oil | 40 | 2800 | 4000 |
| Vegetable Glycerin | | | |
| Glycerin | 45 | 3000 | 4200 |
| Alcohol Blend | | | |
| Alpha-Humulene | 2.5 | 175 | 250 |
| Alpha-Phellandrene | 10 | 700 | 1000 |
| Alpha-pinene | 4.5 | 315 | 450 |
| Alpha-Terpinene | 2.5 | 175 | 250 |
| Alpha-Terpinolene | 26 | 1820 | 2600 |
| Beta-Myrcene | 0.70 | 49 | 70 |
| Beta-pinene | 5 | 350 | 500 |
| Camphene | 0.6 | 42 | 60 |
| Cis-Ocimene | 2 | 140 | 200 |
| Delta-3 Carene | 1.1 | 77 | 110 |
| Limonene | 30 | 2100 | 3000 |
| Sabinene | 2.5 | 175 | 250 |
| Trans-Caryophyllene | 1.40 | 98 | 140 |
| Trans-Ocimene | 1.1 | 77 | 110 |
| γ-Terpinene | 1.5 | 105 | 150 |
| 1.8-Cineole | 1.8 | 126 | 180 |
| Perillyl alcohol | 1 | 70 | 100 |
| Cannabinoids | | | |
| THC-A | 15 | 1050 | 1500 |
| CBD | 4 | 280 | 400 |
| CBDA | 3 | 210 | 300 |
| CBG | 4 | 280 | 400 |
| CBN | 4 | 280 | 400 |
| CBC | 5 | 350 | 500 |
| Whole plant | 1000 | 1500 | 2000 |
| Cold Pressed Plant Oil | | | |
| Oil from Whole Hemp Plant with Seeds Included | 5 | 350 | 500 |
| Omega-6 LA | 7 | 490 | 700 |
| Omega-3 ALA | 2.5 | 175 | 250 |
| Omega-9 | 2 | 140 | 200 |
| Omega-6 GLA | 0.5 | 35 | 500 |
| Omega-3 SDA | 0.25 | 175 | 250 |
| *Astragalus* Extract | | | |
| *Astragalus* | 14 | 980 | 1400 |
| Fenugreek Extract | | | |
| Fenugreek | 5.5 | 385 | 550 |
| Mushroom Extract | | | |
| Red Reishi | 4 | 280 | 400 |
| Shitake | 2 | 140 | 200 |
| Maitake | 2 | 140 | 200 |
| *Ponderosa Armillaria* | 1-2 | 70-140 | 100-200 |
| *Gigantea Calvatia* | 1-2 | 70-140 | 100-200 |
| *Veriscolor Coriolus* | 1-2 | 70-140 | 100-200 |
| *Applanatum Ganoderma* | 1-2 | 70-140 | 100-200 |
| *Velutipes Flammulina* | 1-2 | 70-140 | 100-200 |

In some cases Ajulemic acid is added, or used in place of a cannabinoid. For example, a single serving of the supplement can contain about 1 mg/Kg Ajulemic acid.

Example 4: Healthful Benefits of the CG Medlife Supplement

This Example describes some of the benefits of the CG Medlife Supplement. While it is not presently known whether or not the compositions of the invention deliver curative and/or preventative treatment, these composition have been demonstrated to provide palliative treatment and to lessen the physical and psychological effects of chronic disease states that involve autoimmune conditions, as well as undifferentiated cellular division including but not limited to neoplastic cellular conditions.

Prostate Cancer Patient:

Patient had stage 4 prostate cancer that had metastasized into the bones. The patient's PSA count was as high as 283. Five days after beginning routine administration of CG Medlife Supplement the patient stopped using high powered pain medications that had been prescribed for the cancer pain. The patient continued to go to monthly check-ups and at each check-up the patient's PSA count would go down substantially. After 12 weeks of treatment with the CG Medlife Supplement, the patient was declared to be in remission. No cancer cells were detected in the patient.

Leukemia Patient in New York Hospital:

The patient was diagnosed with stage 4 leukemia. The patient underwent the most advanced treatments for this type of cancer. The first two treatments (IV infusion) were unsuccessful. The doctors said that three such treatments were all they would do. The patient received CG Medlife Supplement for three weeks, with 15 to 20 ml administered over a 24 hour period. The numbers of leukemia cells reduced significantly over the three week period. No other medicines or treatment regimens had accomplished such a reduction. Doctors then decided to try the procedure again even though they truly weren't sure if it would work because it was 4 days outside of the normal success window.

Two and a half weeks later the patient was declared to be in remission. The doctors said there was a 1:30,000 chance of the patient successfully overcoming leukemia in such a short time. He was surprised that it worked at all.

Non-Small Cell Adenocarcinoma

Patient was diagnosed with advanced stage 4 adenocarcinoma (non-small cell). Patient was given 7 to 10 months to live—but that was 9 months ago. Sixteen days ago her daughter called and requested CG Medlife Supplement that she had heard was previously successful. The patient had tried other forms of cannabis unsuccessfully. However, Rick Simpson's oil actually put the patient into the hospital because it had too much THC. Patient was started on 4 milliliters CG Medlife Supplement per night due to her low tolerance. Patient called two days after first receiving CG Medlife Supplement and said she hasn't slept as good as the last two nights in 18 months. The patient had not taken any morphine during those two nights. After three days of receiving CG Medlife Supplement, the patient stopped taking her 3 to 4 OxyContin tablet per day (at least 180 mg per 24 hours).

Patient is now receiving up to 7 ml CG Medlife Supplement over a 24 hour period over the past 12-16 days and she has reported the following:
  No pain
  Gained 7 to 8 pounds
  Cooking again
  Driving again
  Working outside in the garden
  Reporting substantial energy level increases
Patient states that she believes the cancer is receding because she feels so good. She believes that guaranteed death sentence is now in question. She will be going to the doctor soon for testing. Prior to CG Medlife Supplement, she had not been going to the doctor to get check-ups.

Terminal Brain Cancer

Patient had terminal brain cancer, and had gone through chemo treatments previously to put the cancer in remission. Recently the cancer returned and patient states that it is worse now than before. Patient had been experiencing seizures for the last several weeks. His life expectancy was predicted to be less than 2%.

A few days after receiving CG Medlife Supplement, the patient reported that he was sleeping well, had no seizures, and had less shaking of the hands and head. This report was provided after only a few days of receiving the CG Medlife Supplement.

Mitochondrial Disease (Similar to Amyotrophic Lateral Sclerosis)

Patient was diagnosed over a year ago. He was making frequent trips to Boston to try the latest treatment. Some procedures were very painful. He stated that at best some of the treatments only slowed down the progression to a crawl but was still getting worse slowly. Five weeks ago patient started receiving CG Medlife Supplement. Patient reports that:
  80% of feeling is back in his hands and feet
  no pain in the hands and feet
  strength is almost back
  energy level is back almost 100%
  no need to take any of the prescribed 17 pills anymore
  treatment seems to be curing/reversing this so called incurable disease.
Patient's wife reports that he is back for the first time in 18 months.

Crohn's Disease

Patient has had severe Crohn's disease for almost a decade. Several times he actually didn't know if he would survive it because he was so sick. At best, the latest treatments have kept him functioning, but uncomfortably. Five years ago, patient began to experience blurry vision in his right eye, which never went away. The doctor said it was inflammation and that the Crohn's disease spread to his head area. Patient struggled to drive at night because of this.

Patient began receiving CG Medlife Supplement three months ago. After a few days he claimed the following.
  no headaches
  major reduction in cramping
  more regular bowels
After 2 weeks of receiving CG Medlife Supplement the patient reports:
  no cramping
  regular bowels
  eyesight is improving for first time in five years.
Patient states that his life has changed and wants to rely just on CG Medlife Supplement because nothing else has been so beneficial. He said it feels like it is gradually curing him.

Example 5: Healthful Benefits of the Sports Drink/Preventative Supplement

This Example describes some of the benefits of the Sport Drink/Preventative Supplement.

Eczema

A father of three reports that one of his sons has a bad case of eczema. The son has been receiving earlier versions of the Sport Drink/Preventative Supplement for about two years, and over this time period, he has only had a few mild outbreaks.

Healthy Family

The mother of a family of five reports that they have been receiving earlier versions of the Sport Drink/Preventative Supplement for up to five years, and during that time they experienced no health concerns. They have not experienced any lack of energy or even the common cold.

Dog with Hyperadrenocorticism and Other Problems

A boxer at 9 years of age was diagnosed with hyperadrenocorticism, hip dysplasia, arthritis, and enlarged lymph nodes cell tumors. The owners were told to put him to sleep. Instead, the owners took him home and started giving him an earlier version of the Sport Drink/Preventative Supplement. By the age of 10 he was symptom free! The owners were able to keep him in the family until he was 14 years old.

Losing Weight and Increasing Muscle Mass

A 58 year old man uses the Sport Drink/Preventative Supplement. He reports that he is losing weight and regaining lean muscle mass. He states that he is more motivated than ever to get back in shape due to the Sport Drink/Preventative Supplement. He says that he usually get back pains after a workout, but not since he started taking the Sport Drink/Preventative Supplement. Within the last eight months he has lost 32 pounds of fat—not lean muscle.

Smoker with Allergies

Due to years of smoking and increased allergies, a 55 year old woman reports that she was always sick year-round, but since she started taking the Sport Drink/Preventative Supplement this year she feels like she is 23 years old again. Her energy levels have sky-rocketed, and she has not gotten sick since taking the Sport Drink/Preventative Supplement. She says that people have even began to notice the weight she has lost.

Acne and Workout Recovery

A 20-year old male reports that his dad told him to try the Sport Drink/Preventative Supplement, and that is has made a difference in his energy levels. He reports a quicker recovery, and no soreness after a workout or sports. He says it has even cleared up his acne.

As illustrated, even the earlier versions of the Sport Drink/Preventative Supplement exhibit useful properties. The formulation has been improved by adjusting the ingredients and the ratios of ingredients.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various aspects of the invention according to the foregoing description in the specification.

Statements:

1. A CG generic supplement comprising a combination of at least four of the following: vegetable glycerin oil, middle chain-length triacylglycerol oil, fulvic acid minerals/amino acids, raw coconut oil, flavoring, cannabis buds (THC), cannabis leaves (CBD), cannabis plant matter (for acids), cannabis seeds, turmeric root/plant material, sweet wormwood, *Boswellia serrata*, glycine, and hemp seed oil.
2. The CG generic supplement of statement 1, comprising a combination of at least five, or at least seven, or at least nine, or at least ten, or at least eleven, or at least thirteen, or at least fourteen of the following: vegetable glycerin oil, middle chain-length triacylglycerol oil, fulvic acid minerals/amino acids, raw coconut oil, flavoring, cannabis buds (THC), cannabis leaves (CBD), cannabis plant matter (for acids), cannabis seeds, turmeric root/plant material, sweet wormwood, *Boswellia serrata*, glycine, and hemp seed oil.
3. The CG generic supplement of statement 1 or 2, wherein the cannabis buds (THC), cannabis leaves (CBD), cannabis plant matter (for acids), cannabis seeds, turmeric root/plant material, sweet wormwood, and *Boswellia serrata* are whole plants or plant parts that are ground into particles or powder.
4. A method of making a CG generic supplement comprising a combination of the following: vegetable glycerin oil, middle chain-length triacylglycerol oil, fulvic acid minerals/amino acids, raw coconut oil, flavoring, ground cannabis buds (THC), ground cannabis leaves (CBD), ground cannabis plant matter (for acids), ground cannabis seeds, ground turmeric root/plant material, ground sweet wormwood, ground *Boswsellia serrata*, glycine, and hemp seed oil, wherein the method comprises:
    a) mixing together the glycerin (4 parts), medium chain triglycerides (1 part), coconut oil (1 part), and hemp seed oil (2 parts) to form Part 1 oils;
    b) forming Part 2 by mixing about 96 parts of the Part 1 oils with about one-sixth part cannabis buds and 1 part cannabis seeds with heat up to 47-48° C. to thereby form Part 2;
    c) forming Part 3 by mixing about 96 parts of the Part 1 oils with one-sixth part cannabis leaves and 1 part cannabis seeds with heat up to 47-48° C. to thereby form Part 3;
    d) forming Part 4 by mixing about 4 parts fulvic acid with 1 part cannabis plant matter, centrifuging the Part 4 mixture (300-1200 rpm), and retaining the supernatant (removing the debris) as Part 4;
    e) forming Part 5 by mixing together about 110 parts coconut oil, about 1 part flavoring, about 1 part cannabis buds, about 1 part cannabis leaves, about 0.25 part cannabis seeds, about 8 parts glycine, about 20 parts turmeric root/plant, about 28 parts sweet wormwood, and about 20 parts *Boswellia serrata*, and heating this mixture up to 47-48° C., thereby forming Part 5;
    f) forming Part 6 by mixing Part 2 with Part 3, centrifuging (300-1200 rpm) this Part 6 mixture and retaining the supernatant as Part 6;
    g) forming Part 7 by mixing Part 6 with Part 4, centrifuging (300-1200 rpm) the Part 7 mixture, and retaining the supernatant as Part 7;
    h) forming the supplement (Part 8) by mixing Part 7 with Part 5, centrifuging (300-1200 rpm), to generate a supernatant that is the CG Generic Supplement.
5. A CG Medlife supplement comprising at least four of an amino acid blend, a coconut extract, vegetable glycerin, an alcohol blend, a cannabinoid blend, a hemp plant extract, a *Boswellia serrata* extract, a curcuma/turmeric blend, an *Artemisia ludoviciana* extract, a mushroom extract blend, or any combination thereof.
6. The CG Medlife supplement of statement 5, wherein the supplement comprises at least five, or at least six, or at least seven, or at least eight, or at least nine of the following: an amino acid blend, a coconut extract, a vegetable glycerin extract, an alcohol blend, a cannabinoid blend, a hemp plant extract, a *Boswellia serrata* extract, a curcuma/turmeric blend, an *Artemisia ludoviciana* extract, or a mushroom extract blend.
7. The CG Medlife supplement of statement 5 or 6, wherein the supplement comprises all of the following: an amino acid blend, a coconut extract, a vegetable glycerin extract, an alcohol blend, a cannabinoid blend, a hemp plant extract, a *Boswellia serrata* extract, a curcuma/turmeric blend, an *Artemisia ludoviciana* extract, or a mushroom extract blend.
8. The CG Medlife supplement of any of statements 5-7, wherein the amino acid blend comprises alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, minerals, or combinations thereof.
9. The CG Medlife supplement of any of statements 5-8, wherein the amino acid blend contains at least four, or at least five, or at least six, or at least seven, or at least nine, or at least ten, or at least twelve, or at least fourteen, or at least fifteen, or at least seventeen, or at least eighteen of the following: alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, or minerals.
10. The CG Medlife supplement of any of statements 5-9, wherein the amino acid blend comprises (or consists essentially of) all of the following: alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, and minerals.
11. The CG Medlife supplement of any of statements 5-10, wherein the amino acid blend comprises at least five of the following minerals: antimony, barium, beryllium, bismuth, boron, bromine, cadmium, calcium, cerium, cesium, chloride, chromium, cobalt, copper, dysprosium, erbium, europium, fluorine, gadolinium, gallium, germanium, gold, hafnium, holmium, indium, iodine, iridium, iron, lanthanum, lithium, lutetium, magnesium, manganese, molybdenum, neodymium, nickel, niobium, osmium, palladium, phosphorous, platinum, potassium, praseodymium, rhenium, rhodium, rubidium, ruthenium, samarium, scandium, selenium, silicon, silver, sodium, strontium, sulfur, tantalum, tellurium, terbium, thulium, thorium, tin, titanium, tungsten, vanadium, ytterbium, yttrium, zinc, or zirconium.

12. The CG Medlife supplement of any of statements 5-11, wherein the amino acid blend comprises at least seven, or at least ten, or at least fifteen, or at least twenty, or at least thirty, or at least thirty-five, or at least forty, or at least forty-five, or at least fifty, or at least fifty-five, or at least sixty, or at least sixty-five of the following: antimony, barium, beryllium, bismuth, boron, bromine, cadmium, calcium, cerium, cesium, chloride, chromium, cobalt, copper, dysprosium, erbium, europium, fluorine, gadolinium, gallium, germanium, gold, hafnium, holmium, indium, iodine, iridium, iron, lanthanum, lithium, lutetium, magnesium, manganese, molybdenum, neodymium, nickel, niobium, osmium, palladium, phosphorous, platinum, potassium, praseodymium, rhenium, rhodium, rubidium, ruthenium, samarium, scandium, selenium, silicon, silver, sodium, strontium, sulfur, tantalum, tellurium, terbium, thulium, thorium, tin, titanium, tungsten, vanadium, ytterbium, yttrium, zinc, or zirconium.

13. The CG Medlife supplement of any of statements 5-12, wherein a single serving of the supplement contains about 0.1 mg/Kg to about 50 mg/Kg, or from about 0.5 mg/Kg to about 30 mg/Kg, or from about 1 mg/Kg to about 25 mg/Kg of alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, or minerals.

14. The CG Medlife supplement of any of statements 5-13, wherein the coconut extract comprises coconut meat and milk from at least one whole mature coconut, where the meat and milk are ground up together to form a slurry, and heated to up 65° C.

15. The CG Medlife supplement of any of statements 5-14, wherein the coconut extract comprises caprylic acid, coconut oil, middle chain-length triacylglycerols (MCT), or any combination thereof.

16. The CG Medlife supplement of any of statements 5-15, wherein a single serving of the supplement contains about 1 mg/Kg to about 40 mg/Kg. or about 5 mg/Kg to about 30 mg/Kg, or about 10 mg/Kg to about 25 mg/Kg caprylic acid.

17. The CG Medlife supplement of any of statements 5-16, wherein a single serving of the supplement contains about 5 mg/Kg to about 60 mg/Kg, or about 10 mg/Kg to about 50 mg/Kg, or about 15 mg/Kg to about 40 mg/Kg middle chain-length triacylglycerols.

18. The CG Medlife supplement of any of statements 5-17, wherein a single serving of the supplement contains about 10 mg/Kg to about 100 mg/Kg, or about 20 mg/Kg to about 80 mg/Kg, or about 25 mg/Kg to about 60 mg/Kg coconut oil.

19. The CG Medlife supplement of any of statements 5-18, wherein a single serving of the supplement contains about 5 mg/Kg to about 100 mg/Kg, or about 10 mg/Kg to about 80 mg/Kg, or about 20 mg/Kg to about 60 mg/Kg vegetable glycerin.

20. The CG Medlife supplement of any of statements 5-19, wherein the alcohol blend comprises alpha-humulene, alpha-phellandrene, alpha-pinene, alpha-terpinene, alpha-terpinolene, beta-myrcene, beta-pinene, camphene, cis-ocimene, delta-3-carene, limonene, linalool, pulegone, sabinene, trans-caryophyllene, trans-ocimene, gamma-terpinene, α-terpineol, terpineol-4-ol, 1.8-cineole, perillyl alcohol, p-cymene, or any combinations thereof.

21. The CG Medlife supplement of any of statements 5-20, wherein the alcohol blend comprises at least four, or at least five, or at least six, or at least seven, or at least nine, or at least ten, or at least twelve, or at least fifteen, or at least seventeen, or at least nineteen of: alpha-humulene, alpha-phellandrene, alpha-pinene, alpha-terpinene, alpha-terpinolene, beta-myrcene, beta-pinene, camphene, cis-ocimene, delta-3-carene, limonene, linalool, pulegone, sabinene, trans-caryophyllene, trans-ocimene, gamma-terpinene, α-terpineol, terpineol-4-ol, 1.8-cineole, perillyl alcohol, p-cymene, or any combinations thereof.

22. The CG Medlife supplement of any of statements 5-21, wherein the alcohol blend comprises (or consists essentially of): alpha-humulene, alpha-phellandrene, alpha-pinene, alpha-terpinene, alpha-terpinolene, beta-myrcene, beta-pinene, camphene, cis-ocimene, delta-3-carene, limonene, sabinene, trans-caryophyllene, trans-ocimene, gamma-terpinene, 1.8-cineole, and perillyl alcohol.

23. The CG Medlife supplement of any of statements 5-22, wherein a single serving of the supplement contains about 0.01 mg/Kg to about 60 mg/Kg, or about 0.05 mg/Kg to about 50 mg/Kg, or about 0.1 mg/Kg to about 40 mg/Kg of the following: alpha-humulene, alpha-phellandrene, alpha-pinene, alpha-terpinene, alpha-terpinolene, beta-myrcene, beta-pinene, camphene, cis-ocimene, delta-3-carene, limonene, linalool, pulegone, sabinene, trans-caryophyllene, trans-ocimene, gamma-terpinene, α-terpineol, terpineol-4-ol, 1.8-cineole, perillyl alcohol, or p-cymene.

24. The CG Medlife supplement of any of statements 5-23, wherein a single serving of the supplement contains about 0.01 mg/Kg to about 60 mg/Kg, or about 0.05 mg/Kg to about 50 mg/Kg. or about 0.1 mg/Kg to about 40 mg/Kg of the following: alpha-humulene, alpha-phellandrene, alpha-pinene, alpha-terpinene, alpha-terpinolene, beta-myrcene, beta-pinene, camphene, cis-ocimene, delta-3-carene, limonene, sabinene, trans-caryophyllene, trans-ocimene, gamma-terpinene, 1.8-cincole, and perillyl alcohol.

25. The CG Medlife supplement of any of statements 5-24, wherein the cannabinoid blend comprises 9-tetrahydrocannabinol (THC), tetrahydrocannabinolic acid (THC-A), cannabidiol (CBD), cannabidiolic acid (CBDA), cannabigerol (CBG), cannabichromene (CBC), cannabinol (CBN), ajulemic acid, whole cannabis plant material, or any combination thereof.

26. The CG Medlife supplement of any of statements 5-25, wherein the cannabinoid blend comprises at least two, or at least three, or at least four, or at least five, or at least six, or seven of the following: 9-tetrahydrocannabinol (THC), tetrahydrocannabinolic acid (THC-A), cannabidiol (CBD), cannabidiolic acid (CBDA), cannabigerol (CBG), cannabichromene (CBC), cannabinol (CBN), ajulemic acid, or whole cannabis plant material.

27. The CG Medlife supplement of any of statements 5-26, wherein the cannabinoid blend comprises (or consists essentially of) 9-tetrahydrocannabinol (THC), tetrahydrocannabinolic acid (THC-A), cannabidiol (CBD), cannabidiolic acid (CBDA), cannabigerol (CBG), cannabichromene (CBC), cannabinol (CBN), and whole cannabis plant material.
28. The CG Medlife supplement of any of statements 5-27, wherein a single serving of the supplement contains about 1 mg/Kg to about 2000 mg/Kg, or from about 2 mg/Kg to about 1500 mg/Kg, or from about 2 mg/Kg to about 1200 mg/Kg of the following: 9-tetrahydrocannabinol (THC), tetrahydrocannabinolic acid (THC-A), cannabidiol (CBD), cannabidiolic acid (CBDA), cannabigerol (CBG), cannabichromene (CBC), cannabinol (CBN), or whole cannabis plant material.
29. The CG Medlife supplement of any of statements 5-28, wherein a single serving of the supplement contains about 100 mg/Kg to about 2000 mg/Kg, or from about 400 mg/Kg to about 1500 mg/Kg whole cannabis plant material.
30. The CG Medlife supplement of any of statements 5-29, wherein a single serving of the supplement contains about 1 mg/Kg to about 10 mg/Kg of the following: 9-tetrahydrocannabinol (THC), tetrahydrocannabinolic acid (THC-A), cannabidiol (CBD), cannabidiolic acid (CBDA), cannabigerol (CBG), cannabichromene (CBC), or cannabinol (CBN).
31. The CG Medlife supplement of any of statements 5-30, wherein a single serving of the supplement contains about 1 mg/Kg to about 10 mg/Kg of the following: 9-tetrahydrocannabinol (THC), tetrahydrocannabinolic acid (THC-A), cannabidiol (CBD), cannabidiolic acid (CBDA), cannabigerol (CBG), cannabichromene (CBC), and cannabinol (CBN).
32. The CG Medlife supplement of any of statements 5-31, wherein the hemp plant extract comprises hemp oil, omega-6 linoleic acid (omega-6 LA), omega-3 alpha-linoleic acid, gamma-linolenic acid (omega-6 (GLA), stearidonic acid (omega-3 (SDA), omega-9 fatty acids, or any combination thereof.
33. The CG Medlife supplement of any of statements 5-32, wherein the hemp oil extract can contain at least three, at least four, at least five, at least six of the following: hemp oil, omega-6 linoleic acid (omega-6 LA), omega-3 alpha-linoleic acid (omega-3 ALA), gamma-linolenic acid (omega-6 (GLA), stearidonic acid (omega-3 (SDA), or omega-9 fatty acids.
34. The CG Medlife supplement of any of statements 5-33, wherein a single serving of the supplement contains about 0.01 mg/Kg to about 25 mg/Kg. or about 0.05 mg/Kg to about 20 mg/Kg, or about 0.1 mg/Kg to about 15 mg/Kg, or about 0.1 mg/Kg to about 10 mg/Kg of the following: hemp oil, omega-6 linoleic acid (omega-6 LA), omega-3 alpha-linoleic acid (omega-3 ALA), gamma-linolenic acid (omega-6 (GLA), stearidonic acid (omega-3 (SDA), or omega-9 fatty acids.
35. The CG Medlife supplement of any of statements 5-34, wherein the *Boswellia serrata* extract comprises one or more boswellic acids.
36. The CG Medlife supplement of any of statements 5-35, wherein the *Boswellia serrata* extract comprises 1-keto-beta-boswellic acid (KBA), acetyl-1 1-keto-beta-boswellic acid (AKBA), beta-Boswellic acid (BA), acetyl-beta-boswellic acid (ABA), or any combination thereof.
37. The CG Medlife supplement of any of statements 5-36, wherein the *Boswellia serrata* extract comprises 1-keto-beta-boswellic acid (KBA), acetyl-1-keto-beta-boswellic acid (AKBA), beta-Boswellic acid (BA), and acetyl-beta-boswellic acid (ABA).
38. The CG Medlife supplement of any of statements 5-37, wherein the *Boswellia serrata* extract comprises resin or gum tapped from the incision made on the trunk of the tree that is extracted with C1-C6 alcohol at a temperature up to 68-70° C., removal of the alcohol, treatment with alkali at a temperature ranging from room temperature to 50° C. (e.g., 5% by weight aqueous KOH), wash with ethyl acetate and remove the ethyl acetate, collection of the aqueous layer, treatment of the aqueous layer with hydrochloric acid to lower the pH to about pH 4, collection of a precipitate that forms, and washing of the precipitate with water.
39. The CG Medlife supplement of any of statements 5-38, wherein a single serving of the supplement contains about 5 mg/Kg to about 100 mg/Kg, or from about 10 mg/Kg to about 80 mg/Kg, or from about 20 mg/Kg to about 65 mg/Kg of *Boswellia serrata* extract.
40. The CG Medlife supplement of any of statements 5-39, wherein the curcuma/turmeric blend comprises ground whole turmeric (*Curcuma longa*) plants, or turmeric plant parts.
41. The CG Medlife supplement of any of statements 5-40, wherein the curcuma/turmeric blend comprises ground *Curcuma longa* rhizomes.
42. The CG Medlife supplement of any of statements 5-41, wherein the curcuma/turmeric blend comprises an alcohol/water extract of ground *Curcuma longa* that can be dried or concentrated.
43. The CG Medlife supplement of any of statements 5-42, wherein a single serving of the supplement contains about 0.1 mg/Kg to about 20 mg/Kg, or about 0.5 mg/Kg to about 14 mg/Kg, or about 1 mg/Kg to about 8 mg/Kg turmeric.
44. The CG Medlife supplement of any of statements 5-43, wherein the *Artemisia ludoviciana* extract comprises whole *Artemisia ludoviciana* plants or *Artemisia ludoviciana* plants parts.
45. The CG Medlife supplement of any of statements 5-44, wherein the *Artemisia ludoviciana* extract comprises whole *Artemisia ludoviciana* and/or *Artemisia princeps* plants, or parts of *Artemisia ludoviciana* and/or *Artemisia princeps* plants.
46. The CG Medlife supplement of any of statements 5-45, wherein the *Artemisia ludoviciana* extract comprises whole *Artemisia ludoviciana* leaves.
47. The CG Medlife supplement of any of statements 5-46, wherein dried *Artemisia ludoviciana* and/or *Artemisia princeps* leaves are washed with water, the leaves are allowed to stand in water at room temperature for several days, the leaves and water are centrifuged with retention of supernatant, the centrifuged sediment is washed with water, with retention of the supernatant, the supernatants are all combined, the combined supernatants are size-fractionated with retention of substances having a molecular weight of more than 200,000 g/mole to generate an aqueous *Artemisia ludoviciana* extract, and the aqueous *Artemisia ludoviciana* extract is dried to generate a dry *Artemisia ludoviciana* extract.
48. The CG Medlife supplement of any of statements 5-47, wherein a single serving of the supplement contains about 0.1 mg/Kg to about 20 mg/Kg, or from about 0.5 mg/Kg to about 15 mg/Kg, or from about 1 mg/Kg to about 10 mg/Kg *Artemisia ludoviciana* and/or *Artemisia princeps* extract.
49. The CG Medlife supplement of any of statements 5-48, wherein the mushroom extract blend comprises mushrooms or parts of mushrooms, such as the caps.

50. The CG Medlife supplement of any of statements 5-49, wherein the mushroom extract blend comprises ground Red Reishi, Shitake, Maitake, *Ponderosa armillaria, Gigantea calvatia, Veriscolor coriolus, Applanatum ganoderma, Velutipes flammulina*, or any combination thereof.
51. The CG Medlife supplement of any of statements 5-50, wherein the mushroom extract blend comprises at least two, or at least three, or at least four, or at least five of these mushroom extracts, or at least six, or seven of the following: ground Red Reishi, Shitake, Maitake, *Ponderosa armillaria, Gigantea calvatia, Veriscolor coriolus, Applanatum ganoderma*, or *Velutipes flammulina*.
52. The CG Medlife supplement of any of statements 5-51, wherein a single serving of the supplement contains about 0.01 mg/Kg to about 20 mg/Kg, or from about 0.05 mg/Kg to about 10 mg/Kg, or from about 0.1 mg/Kg to about 8 mg/Kg ground Red Reishi, Shitake, Maitake, *Ponderosa armillaria, Gigantea calvatia, Veriscolor coriolus, Applanatum ganoderma*, or *Velutipes flammulina*.
53. The CG Medlife supplement of any of statements 5-52, formulated by a process that comprises one or more of the following: grinding solids, cold-pressing plant materials to obtain oils, mixing solids with oil-containing or waxy components, heating up to 60° C., preparing one or more homogenates, mixing two or more homogenates, extracting with glycerin or oil-containing components, or centrifuging to remove debris.
54. A Sports Drink/Preventative supplement comprising at least four of an amino acid blend, a coconut extract, vegetable glycerin, an alcohol blend, a cannabinoid blend, a hemp plant extract, an *Artragalus* extract, a fenugreek extract, a mushroom extract blend, or any combination thereof.
55. The Sports Drink/Preventative supplement of statement 54, wherein the supplement comprises at least five, or at least six, or at least seven, or at least eight, or nine of the following: an amino acid blend, a coconut extract, vegetable glycerin, an alcohol blend, a cannabinoid blend, a hemp plant extract, an *Artragalus* extract, a fenugreek extract, a mushroom extract blend.
56. The Sports Drink/Preventative supplement of statement 54 or 55, wherein the supplement contains no added tetrahydrocannabinol (THC).
57. The Sports Drink/Preventative supplement of any of statements 54-56, wherein the supplement contains no tetrahydrocannabinol (THC), or only a non-psychoactive amount of tetrahydrocannabinol (THC).
58. The Sports Drink/Preventative supplement of any of statements 54-57, wherein the amino acid blend comprises alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, minerals, or any combination thereof.
59. The Sports Drink/Preventative supplement of any of statements 54-58, wherein the amino acid blend contains at least four, or at least five, or at least six, or at least seven, or at least nine, or at least ten, or at least twelve, or at least fourteen, or at least fifteen, or at least seventeen, or at least eighteen of the following: alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, or minerals.
60. The Sports Drink/Preventative supplement of any of statements 54-59, wherein the amino acid blend comprises (or consists essentially of) all of the following: alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, and minerals.
61. The Sports Drink/Preventative supplement of any of statements 54-60, wherein the amino acid blend comprises at least five of the following: antimony, barium, beryllium, bismuth, boron, bromine, cadmium, calcium, cerium, cesium, chloride, chromium, cobalt, copper, dysprosium, erbium, europium, fluorine, gadolinium, gallium, germanium, gold, hafnium, holmium, indium, iodine, iridium, iron, lanthanum, lithium, lutetium, magnesium, manganese, molybdenum, neodymium, nickel, niobium, osmium, palladium, phosphorous, platinum, potassium, praseodymium, rhenium, rhodium, rubidium, ruthenium, samarium, scandium, selenium, silicon, silver, sodium, strontium, sulfur, tantalum, tellurium, terbium, thulium, thorium, tin, titanium, tungsten, vanadium, ytterbium, yttrium, zinc, or zirconium.
62. The Sports Drink/Preventative supplement of any of statements 54-61, wherein the amino acid blend comprises at least seven, or at least ten, or at least fifteen, or at least twenty, or at least thirty, or at least thirty-five, or at least forty, or at least forty-five, or at least fifty, or at least fifty-five, or at least sixty, or at least sixty-five of the following: antimony, barium, beryllium, bismuth, boron, bromine, cadmium, calcium, cerium, cesium, chloride, chromium, cobalt, copper, dysprosium, erbium, europium, fluorine, gadolinium, gallium, germanium, gold, hafnium, holmium, indium, iodine, iridium, iron, lanthanum, lithium, lutetium, magnesium, manganese, molybdenum, neodymium, nickel, niobium, osmium, palladium, phosphorous, platinum, potassium, praseodymium, rhenium, rhodium, rubidium, ruthenium, samarium, scandium, selenium, silicon, silver, sodium, strontium, sulfur, tantalum, tellurium, terbium, thulium, thorium, tin, titanium, tungsten, vanadium, ytterbium, yttrium, zinc, or zirconium.
63. The Sports Drink/Preventative supplement of any of statements 54-62, wherein a single serving of the supplement contains about 0.1 mg/Kg to about 50 mg/Kg, or from about 0.5 mg/Kg to about 30 mg/Kg, or from about 1 mg/Kg to about 25 mg/Kg of alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, or minerals.
64. The Sports Drink/Preventative supplement of any of statements 54-63, wherein a single serving of the supplement contains about 0.1 mg/Kg to about 50 mg/Kg, or from about 0.5 mg/Kg to about 30 mg/Kg, or from about 1 mg/Kg to about 25 mg/Kg of alanine, arginine, aspartic acid, cystine, glutamic acid, glycine, histidine, isoleucine, lysine, leucine, methionine, phenylalanine, serine, proline, threonine, tryptophan, tyrosine, valine, fulvic-humic acids, and minerals.
65. The Sports Drink/Preventative supplement of any of statements 54-64, wherein the coconut extract comprises coconut meat and milk from at least one whole mature coconut, where the meat and milk are ground up together to form a slurry, and heated to up 65° C.
66. The Sports Drink/Preventative supplement of any of statements 54-65, wherein the coconut extract comprises caprylic acid, coconut oil, middle chain-length triacylglycerols (MCT), or any combination thereof.
67. The Sports Drink/Preventative supplement of any of statements 54-66, wherein a single serving of the supplement contains about 1 mg/Kg to about 40 mg/Kg, or about 5 mg/Kg to about 30 mg/Kg, or about 10 mg/Kg to about 25 mg/Kg caprylic acid.
68. The Sports Drink/Preventative supplement of any of statements 54-67, wherein a single serving of the supplement contains about 5 mg/Kg to about 60 mg/Kg, or about 10 mg/Kg to about 50 mg/Kg, or about 15 mg/Kg to about 40 mg/Kg middle chain-length triacylglycerols.
69. The Sports Drink/Preventative supplement of any of statements 54-68, wherein a single serving of the supplement contains about 10 mg/Kg to about 100 mg/Kg, or about 20 mg/Kg to about 80 mg/Kg, or about 25 mg/Kg to about 60 mg/Kg coconut oil.
70. The Sports Drink/Preventative supplement of any of statements 54-69, wherein a single serving of the supplement contains about 5 mg/Kg to about 100 mg/Kg, or about 10 mg/Kg to about 80 mg/Kg, or about 20 mg/Kg to about 60 mg/Kg vegetable glycerin.
71. The Sports Drink/Preventative supplement of any of statements 54-70, wherein the alcohol blend comprises alpha-humulene, alpha-phellandrene, alpha-pinene, alpha-terpinene, alpha-terpinolene, beta-myrcene, beta-pinene, camphene, cis-ocimene, delta-3-carene, limonene, linalool, pulegone, sabinene, trans-caryophyllene, trans-ocimene, gamma-terpinene, α-terpineol, terpineol-4-ol, 1.8-cineole, perillyl alcohol, p-cymene, or any combination thereof.
72. The Sports Drink/Preventative supplement of any of statements 54-71, wherein the alcohol blend comprises at least four, or at least five, or at least six, or at least seven, or at least nine, or at least ten, or at least twelve, or at least fifteen, or at least seventeen, or at least nineteen of: alpha-humulene, alpha-phellandrene, alpha-pinene, alpha-terpinene, alpha-terpinolene, beta-myrcene, beta-pinene, camphene, cis-ocimene, delta-3-carene, limonene, linalool, pulegone, sabinene, trans-caryophyllene, trans-ocimene, gamma-terpinene. α-terpineol, terpineol-4-ol, 1.8-cineole, perillyl alcohol, p-cymene, or any combinations thereof.
73. The Sports Drink/Preventative supplement of any of statements 54-72, wherein the alcohol blend comprises (or consists essentially of): alpha-humulene, alpha-phellandrene, alpha-pinene, alpha-terpinene, alpha-terpinolene, beta-myrcene, beta-pinene, camphene, cis-ocimene, delta-3-carene, limonene, sabinene, trans-caryophyllene, trans-ocimene, gamma-terpinene, 1.8-cineole, and perillyl alcohol.
74. The Sports Drink/Preventative supplement of any of statements 54-73, wherein a single serving of the supplement contains about 0.01 mg/Kg to about 60 mg/Kg, or about 0.05 mg/Kg to about 50 mg/Kg, or about 0.1 mg/Kg to about 40 mg/Kg of the following: alpha-humulene, alpha-phellandrene, alpha-pinene, alpha-terpinene, alpha-terpinolene, beta-myrcene, beta-pinene, camphene, cis-ocimene, delta-3-carene, limonene, linalool, pulegone, sabinene, trans-caryophyllene, trans-ocimene, gamma-terpinene, α-terpineol, terpincol-4-ol, 1.8-cincole, perillyl alcohol, or p-cymene.
75. The Sports Drink/Preventative supplement of any of statements 54-74, wherein a single serving of the supplement contains about 0.01 mg/Kg to about 60 mg/Kg, or about 0.05 mg/Kg to about 50 mg/Kg, or about 0.1 mg/Kg to about 40 mg/Kg of the following: alpha-humulene, alpha-phellandrene, alpha-pinene, alpha-terpinene, alpha-terpinolene, beta-myrcene, beta-pinene, camphene, cis-ocimene, delta-3-carene, limonene, sabinene, trans-caryophyllene, trans-ocimene, gamma-terpinene, 1.8-cincole, and perillyl alcohol.
76. The Sports Drink/Preventative supplement of any of statements 54-75, wherein the cannabinoid blend comprises tetrahydrocannabinolic acid (THC-A), cannabidiol (CBD), cannabidiolic acid (CBDA), cannabigerol (CBG), cannabichromene (CBC), cannabinol (CBN), ajulemic acid, whole cannabis plant material, or any combination thereof.
77. The Sports Drink/Preventative supplement of any of statements 54-76, wherein the cannabinoid blend comprises at least two, or at least three, or at least four, or at least five, or at least six, or seven of the following: tetrahydrocannabinolic acid (THC-A), cannabidiol (CBD), cannabidiolic acid (CBDA), cannabigerol (CBG), cannabichromene (CBC), cannabinol (CBN), ajulemic acid, or whole cannabis plant material.
78. The Sports Drink/Preventative supplement of any of statements 54-77, wherein the cannabinoid blend contains no added 9-tetrahydrocannabinol (THC).
79. The Sports Drink/Preventative supplement of any of statements 54-78, wherein the cannabinoid blend contains non-psychoactive amounts of 9-tetrahydrocannabinol (THC), no detectable amounts of 9-tetrahydrocannabinol (THC), or no 9-tetrahydrocannabinol (THC).
80. The Sports Drink/Preventative supplement of any of statements 54-79, wherein a single serving of the supplement contains about 1 mg/Kg to about 2000 mg/Kg. or from about 2 mg/Kg to about 1500 mg/Kg. or from about 2 mg/Kg to about 1200 mg/Kg of the following: tetrahydrocannabinolic acid (THC-A), cannabidiol (CBD), cannabidiolic acid (CBDA), cannabigerol (CBG), cannabichromene (CBC), cannabinol (CBN), or whole cannabis plant material.
81. The Sports Drink/Preventative supplement of any of statements 54-80, wherein a single serving of the supplement contains about 100 mg/Kg to about 2000 mg/Kg. or from about 400 mg/Kg to about 1500 mg/Kg whole cannabis plant material.
82. The Sports Drink/Preventative supplement of any of statements 54-81, wherein a single serving of the supplement contains about 1 mg/Kg to about 10 mg/Kg of the following: tetrahydrocannabinolic acid (THC-A), cannabidiol (CBD), cannabidiolic acid (CBDA), cannabigerol (CBG), cannabichromene (CBC), or cannabinol (CBN).
83. The Sports Drink/Preventative supplement of any of statements 54-82, wherein a single serving of the supplement contains about 1 mg/Kg to about 10 mg/Kg of the following: tetrahydrocannabinolic acid (THC-A), cannabidiol (CBD), cannabidiolic acid (CBDA), cannabigerol (CBG), cannabichromene (CBC), and cannabinol (CBN).
84. The Sports Drink/Preventative supplement of any of statements 54-83, wherein the hemp plant extract comprises hemp oil, omega-6 linoleic acid (omega-6 LA), omega-3 alpha-linoleic acid, gamma-linolenic acid (omega-6 (GLA), stearidonic acid (omega-3 (SDA), omega-9 fatty acids, or any combination thereof.
85. The Sports Drink/Preventative supplement of any of statements 54-84, wherein the hemp oil extract can contain at least three, at least four, at least five, at least six of the following: hemp oil, omega-6 linoleic acid (omega-6 LA), omega-3 alpha-linoleic acid (omega-3 ALA), gamma-linolenic acid (omega-6 (GLA), stearidonic acid (omega-3 (SDA), or omega-9 fatty acids.

86. The Sports Drink/Preventative supplement of any of statements 54-85, wherein a single serving of the supplement contains about 0.01 mg/Kg to about 25 mg/Kg, or about 0.05 mg/Kg to about 20 mg/Kg, or about 0.1 mg/Kg to about 15 mg/Kg, or about 0.1 mg/Kg to about 10 mg/Kg of the following: hemp oil, omega-6 linoleic acid (omega-6 LA), omega-3 alpha-linoleic acid (omega-3 ALA), gamma-linolenic acid (omega-6 GLA), stearidonic acid (omega-3 SDA), or omega-9 fatty acids.

87. The Sports Drink/Preventative supplement of any of statements 54-86, wherein the *Astragalus* extract is an *Astragalus membranaceus* extract.

88. The Sports Drink/Preventative supplement of any of statements 54-87, wherein the *Astragalus* extract comprises ground whole plant *Astragalus*, or an extracted polysaccharide mixture containing *Astragalus* substances with molecular weights ranging from 12,000 to 500,000 daltons.

89. The Sports Drink/Preventative supplement of any of statements 54-88, wherein each serving contains about 1 mg/Kg to about 30 mg/Kg, or from about 3 mg/Kg to about 25 mg/Kg, or from about 5 mg/Kg to about 20 mg/Kg *Astragalus* extract.

90. The Sports Drink/Preventative supplement of any of statements 54-89, wherein the fenugreek extract comprises ground whole fenugreek plants, parts of fenugreek plants, or fenugreek seeds.

91. The Sports Drink/Preventative supplement of any of statements 54-90, wherein the fenugreek extract comprises ground fenugreek seeds.

92. The Sports Drink/Preventative supplement of any of statements 54-91, wherein the fenugreek extract is generated by grinding fenugreek seeds, removing lipophilic compounds by hexane extraction to generate a defatted powder, boiling the defatted powder in ethanol, soaking then stirring the powder in water with pH 3.5 to generate a slurry, filtering the slurry, retaining the filtrate, centrifuging the filtrate and removing the sediment to generate a supernatant, concentrating the supernatant to about 50% of its initial volume, mixing the concentrated supernatant solution with the same volume of 96% ethanol, storing the mixture in a refrigerator to generate a precipitated mucilage, collecting the precipitated mucilage by centrifugation, re-suspending and mixing the precipitated mucilage in distilled water to remove impurities, re-precipitating the precipitated mucilage, washing the precipitated mucilage with diethyl ether and acetone, and drying the precipitated mucilage to generate an off-white powder which is the fenugreek extract.

93. The Sports Drink/Preventative supplement of any of statements 54-92, wherein each serving contains about 0.1 mg/Kg to about 20 mg/Kg, or from about 0.5 mg/Kg to about 15 mg/Kg, or from about 1 mg/Kg to about 10 mg/Kg fenugreek extract.

94. The Sports Drink/Preventative supplement of any of statements 54-93, wherein the mushroom extract blend comprises mushrooms or parts of mushrooms, such as the caps.

95. The Sports Drink/Preventative supplement of any of statements 54-94, wherein the mushroom extract blend comprises ground Red Reishi, Shitake. Maitake, *Ponderosa armillaria, Gigantea calvatia, Veriscolor coriolus, Applanatum ganoderma, Velutipes flammulina*, or any combination thereof.

96. The Sports Drink/Preventative supplement of any of statements 54-95, wherein the mushroom extract blend comprises at least two, or at least three, or at least four, or at least five of these mushroom extracts, or at least six, or seven of the following: ground Red Reishi, Shitake, Maitake, *Ponderosa armillaria, Gigantea calvatia, Veriscolor coriolus, Applantum ganoderma*, or *Velutipes flammulina*.

97. The Sports Drink/Preventative supplement of any of statements 54-96, wherein a single serving of the supplement contains about 0.01 mg/Kg to about 20 mg/Kg, or from about 0.05 mg/Kg to about 10 mg/Kg, or from about 0.1 mg/Kg to about 8 mg/Kg ground Red Reishi, Shitake, Maitake, *Ponderosa armillaria, Gigantea* calvatia, *Veriscolor coriolus, Applanatum ganoderma*, or *Velutipes flammulina*.

98. The Sports Drink/Preventative supplement of any of statements 54-97, formulated by a process that comprises one or more of the following: grinding solids, cold-pressing plant materials to obtain oils, mixing solids with oil-containing or waxy components, heating up to 60° C., preparing one or more homogenates, mixing two or more homogenates, extracting with glycerin or oil-containing components, or centrifuging to remove debris.

99. The supplement of any of statements 1-98, wherein the supplement has a mildly alkaline pH, for example, about pH 7.0 to about pH 7.8.

100. The supplement of any of statements 1-99, wherein the supplement is a liquid.

101. The supplement of any of statements 1-100, wherein a single serving of the supplement is about 0.25 fluid ounces to about 12 fluid ounces, or about 0.5 fluid ounces to about 8 fluid ounces, or 1 fluid ounces to about 6 fluid ounces.

102. A method of optimizing health in an animal comprising administering the supplement of any of statements 1-101 to the animal at least once per week for four weeks, to thereby optimize the health of the animal.

103. The method of statement 102, wherein the animal is a human, a domesticated animal, or a zoo animal.

104. The method of statement 102 or 103 wherein optimizing health of the animal comprises reducing the incidence or severity of disease compared to an animal of the same species that does not receive the supplement.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound," "a cell," "a nutrient" or "an amino acid" includes a plurality of such compounds, cells, nutrients or amino acids (for example, a solution of cells, nutrients, or amino acids, a suspension of cells, or a series of compound, nutrient, or amino acid preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A supplement comprising amino acids, alcohol blend, cannabinoid, hemp, pumpkin seed extract and mushrooms formulated in capsule or tablet form;
   a) wherein the amino acids are a blend of the following: alanine, arginine, aspartic acid, cystine, glutamic acid, histidine, isoleucine, lysine, leucine, methionine, phenylalanine, serine, proline, threonine, tyrosine, valine, fulvic-humic acids, and minerals;
   b) wherein the alcohol blend comprising alpha-humulene, alpha-pinene, beta-myrcene, beta-pinene, camphene, delta-3-carene, limonene, or linalool;
   c) wherein the cannabinoid comprises: 9-tetrahydrocannabinol (THC),-tetrahydrocannabinolic acid (THC-A), cannabidiol (CBD), cannabidiolic add (CBDA), cannabigerol (CBG), cannabichromene (CBC), cannabinol (CBN), or ajulemic acid;
   d) wherein the hemp is a hemp plant extract or a hemp oil extract comprising hemp oil, omega-6 linoleic acid (omega-6 LA), omega-3 alpha-linoleic acid (omega-3 ALA), gamma-linolenic acid (omega-6 (GLA), stearidonic acid (omega-3 (SDA), or omega-9 fatty acids or a combination thereof; and
   e) wherein the mushrooms comprise Red Reishi, Shitake, Maitake, *Coriolus versicolor, Ganoderma applanatum*, and *Flammulina velutipes*.

2. A method comprising administering the supplement of claim 1 to a subject.

3. A supplement comprising an amino acid blend, an alcohol blend, a cannabinoid blend, a hemp plant extract, a fenugreek extract, pumpkin seed powder, and a mushroom blend comprising Red Reishi, Shitake, Maitake, *Coriolus versicolor, Ganoderma applanatum*, and *Flammulina velutipes* formulated in capsule or tablet form.

4. The supplement of claim 3;
   a) wherein the amino acid blend comprises: alanine, arginine, aspartic acid, cystine, glutamic acid, histidine, isoleucine, lysine, leucine, methionine, phenylalanine, serine, proline, threonine, tyrosine, valine, fulvic-humic acids, and minerals;
   b) wherein the alcohol blend comprises: alpha-humulene, alpha-phellandrene, alpha-pinene, alpha-terpinolene, beta-myrcene, or beta-pinene;
   c) wherein the cannabinoid blend comprises cannabidiol (CBD) or 9-tetrahydrocannabinol (THC).

5. The supplement of claim 4 further comprising one or more vitamins.

6. The supplement of claim 4 further comprising a preservative, coloring agent, flavoring, or a combination thereof.

7. The supplement of claim 4, in liquid form.

8. A supplement formulated in capsule or tablet form comprising an amino acid blend, an alcohol blend, a cannabinoid blend, a fenugreek extract, pumpkin seed powder, and a mushroom blend comprising Red Reishi, Shitake, Maitake, *Coriolus versicolor, Ganoderma applanatum*, and *Flammulina velutipes*.

9. A supplement formulated in capsule or tablet form comprising an amino acid blend, a cannabinoid blend, a fenugreek extract, pumpkin seed powder, and a mushroom blend comprising Red Reishi, Shitake, Maitake, *Coriolus versicolor, Ganoderma applanatum*, and *Flammulina velutipes*.

* * * * *

UNITED STATES PATENT AND TRADEMARK OFFICE
CERTIFICATE OF CORRECTION

PATENT NO. : 11,369,655 B2
APPLICATION NO. : 15/742242
DATED : June 28, 2022
INVENTOR(S) : George et al.

It is certified that error appears in the above-identified patent and that said Letters Patent is hereby corrected as shown below:

On the Title Page

On page 2, in Column 2, under item (56) "Other Publications", Line 19, delete "Alkaierini," and insert --Alkaterini,-- therefor In the Claims In Column 47, Line 38, in Claim 1, delete "add" and insert --acid-- therefor Signed and Sealed this
Sixteenth Day of August, 2022

Katherine Kelly Vidal
*Director of the United States Patent and Trademark Office*